(12) United States Patent
Quist

(10) Patent No.: US 7,154,596 B2
(45) Date of Patent: *Dec. 26, 2006

(54) METHOD AND APPARATUS FOR BACKLIGHTING AND IMAGING MULTIPLE VIEWS OF ISOLATED FEATURES OF AN OBJECT

(76) Inventor: Bradley L. Quist, 17137 Jonquil Ave., Lakeville, MN (US) 55044

( * ) Notice: Subject to any disclaimer, the term of this patent is extended or adjusted under 35 U.S.C. 154(b) by 0 days.

This patent is subject to a terminal disclaimer.

(21) Appl. No.: 11/374,223

(22) Filed: Mar. 13, 2006

(65) Prior Publication Data

US 2006/0152741 A1 Jul. 13, 2006

Related U.S. Application Data

(63) Continuation of application No. 10/868,051, filed on Jun. 15, 2004, now Pat. No. 7,012,682, which is a continuation of application No. 10/099,684, filed on Mar. 15, 2002, now Pat. No. 6,813,016.

(51) Int. Cl.
*G01N 21/00* (2006.01)

(52) U.S. Cl. ............... 356/237.1; 356/614; 250/559.08

(58) Field of Classification Search .. 356/237.1–237.6, 356/614–615, 390; 250/559.08, 559.23, 250/559.34, 559.44, 559.46; 382/145, 151
See application file for complete search history.

(56) References Cited

U.S. PATENT DOCUMENTS

| | | | |
|---|---|---|---|
| 4,654,949 A | | 4/1987 | Pryor |
| 4,875,778 A | * | 10/1989 | Luebbe et al. ............... 356/394 |
| 4,959,898 A | | 10/1990 | Landman et al. |
| 5,043,589 A | * | 8/1991 | Smedt et al. .......... 250/559.08 |
| 5,061,895 A | | 10/1991 | Fong |
| 5,131,753 A | | 7/1992 | Pine et al. |
| 5,140,643 A | * | 8/1992 | Izumi et al. ................. 382/153 |
| 5,249,239 A | * | 9/1993 | Kida ........................... 382/146 |
| 5,452,080 A | | 9/1995 | Tomiya |
| 5,563,703 A | | 10/1996 | Lebeau et al. |
| 5,621,530 A | | 4/1997 | Marrable, Jr. |
| 5,812,269 A | | 9/1998 | Svetkoff et al. |
| 5,812,693 A | | 9/1998 | Burt et al. |
| 5,864,405 A | | 1/1999 | Ikeno |
| 5,872,051 A | | 2/1999 | Fallon et al. |
| 5,909,285 A | | 6/1999 | Beaty et al. |
| 5,995,220 A | | 11/1999 | Suzuki |

(Continued)

*Primary Examiner*—Sang H. Nguyen
(74) *Attorney, Agent, or Firm*—Charles A. Lemaire; Lemaire Patent Law Firm, P.L.L.C.

(57) ABSTRACT

Manufacturing lines include inspection systems for monitoring the quality of parts produced. Manufacturing lines for making semiconductor devices generally inspect each fabricated part. The information obtained is used to fix manufacturing problems in the semiconductor fab plant. A machine-vision system for imaging an object having a first side and a second side includes an imager, and an optics apparatus that images two or more views of the first side of the object and images two or more views of the second side of the object. The two or more views of the first side and the second side of the object are each from different angles. The object includes at least one major surface. A divider background surface is placed near the at least one major surface of the object to obtain separate images of features of the object on the first side of the object and features of the object on the second side of the object. In one embodiment, the divider diffuses light to back light the features on the object on the first side and back light the features on the second side of the object.

27 Claims, 15 Drawing Sheets

U.S. PATENT DOCUMENTS

| | | |
|---|---|---|
| 6,075,883 A | 6/2000 | Stern et al. |
| 6,084,631 A | 7/2000 | Tonkin et al. |
| 6,141,040 A | 10/2000 | Toh |
| 6,163,946 A | 12/2000 | Pryor |
| 6,165,885 A | 12/2000 | Gaynes et al. |
| 6,242,756 B1 | 6/2001 | Toh et al. |
| 6,243,164 B1 | 6/2001 | Baldwin et al. |
| 6,307,210 B1 | 10/2001 | Suzuki et al. |
| 6,518,997 B1 | 2/2003 | Chow et al. |
| 6,532,063 B1 * | 3/2003 | Tan et al. ................ 356/237.1 |
| 6,573,987 B1 * | 6/2003 | Shires ..................... 356/237.2 |
| 6,713,311 B1 | 3/2004 | Wong |
| 7,012,682 B1 * | 3/2006 | Quist ..................... 356/237.1 |

* cited by examiner

OBJECT PART SKEWED SO ALL PINS SEPARATELY IMAGED FROM SIDE VIEW

METHOD AND APPARATUS FOR BACKLIGHTING AND IMAGING MULTIPLE VIEWS OF ISOLATED FEATURES OF AN OBJECT

CROSS-REFERENCE TO RELATED APPLICATIONS

This invention is a continuation of U.S. patent application Ser. No. 10/868,051 filed Jun. 15, 2004 now U.S. Pat. No. 7,012,682; which is a continuation U.S. patent application Ser. No. 10/099,684 filed Mar. 15, 2002 (now U.S. Pat. No. 6,813,016); which applications are hereby incorporated by reference in entirety.

FIELD OF THE INVENTION

This invention relates to the field of machine vision, and more specifically to a mechanical apparatus and method for obtaining inspection data for parts in a manufacturing environment. More particularly, the present invention relates to obtaining inspection data for two sides, edges, or surfaces of a part and displaying the same on an imaging device.

BACKGROUND OF THE INVENTION

There is a widespread need for inspection data for electronic parts in a manufacturing environment. One common inspection method uses a video camera to acquire two-dimensional images of a device-under-test. Current systems have problems. The problems include the inability of getting separated images of portions of the electronic part. To inspect leads on a part, the leads are lighted from the front. One row of leads, solder balls, or pins, for example, along an edge of the part, are lighted from the front and focused on, so that the row of leads on the opposite edge are out of focus thus allowing geometric measurement of the nearby leads. When electrical leads or other shiny surfaces are viewed using front lighting specular reflections result. Portions of the part causing specular reflections generally can not be measured or handled by an optical system. Elimination of specular reflections requires backlighting of the parts. In current inspection systems, backlighting has a problem since the various features to be viewed are not separated. For example, viewing a first row of leads along an edge also shows another row of leads on an opposite edge. The result is that the information sought, such as co-planarity and other critical parameters may not be accurately obtained since the features behind a critical portion of the object or device under test can not be viewed separately. In other words, the data collected on backlit parts may be bad since another portion of the device under test may introduce error in the measurement of the part.

U.S. Pat. No. 6,141,040 entitled "Measurement and Inspection of Leads on Integrated Circuit Packages" and issued to Toh discusses an arrangement of optics, cameras and an image processor for capturing images of lead tips of object fields resulting in accurate three dimensional positions of all the leads on a integrated circuit such as a Quad Flat Package (QFP). The system includes a telecentric lens attached to a camera working with an arrangement of mirrors and lighting. The telecentric lens and mirror optical layout splits the acquired image into 2 orthogonal viewing fields of the same lead tips of the QFP. The QFP is placed flat on a pedestal, and for any given side of the QFP, the first field views the lead tips from the front. The second field views the lead tips from the bottom of the IC package. Lead tip images are acquired by a lighting arrangement that casts illumination on the lead tips only. Electronic processing techniques are used to compute the geometry of the leads such as global co-planarity, lead standoff and inspection of other lead defects. This invention only provides views of leads on one side of a package. In addition, the leads are illuminated from the side facing the camera rather than back lighting the leads.

U.S. Pat. No. 6,243,164 entitled "Method and System for Determining Co-planarity" and issued to Baldwin, et al. discloses another system. The co-planarity of leads of an integrated circuit (IC) in a surface-mount technology package (SMT) can be determined by means of a plurality of views without the use of a conventional pedestal, without the use of an associated Z-axis actuator, and without the associated delays required to deploy such a Z-axis actuator. In the invention, three leads of SMT package are arbitrarily selected to define a virtual reference plane in a first or virtual coordinate system, and the positions of the unselected leads are measured with reference to the virtual reference plane. For convenience, the virtual reference plane can be defined as Z=0 and may have height coordinates in Z that are negative or positive with respect to the virtual reference plane. The virtual coordinates are analyzed, and three leads having the lowest Z coordinates are determined to define a virtual sitting plane. For convenience, the virtual sitting plane can be defined as Z=0 in a second or real coordinate system. A mathematical transformation that relates the first coordinate system to the second coordinate system is determined, and the coordinates for each lead of SMT package are subsequently transformed from the first coordinate system to the second coordinate system. In the second coordinate system, each Z coordinate directly corresponds to the lead standoff value that largely determines the acceptability of the inspected SMT package. A variety of techniques are optionally employed to determine whether SMT package is bi-stable.

U.S. Pat. No. 4,959,898 entitled "Surface Mount Machine with Lead Coplanarity Verifier" and issued to Landman, et al. discloses an apparatus for performing a non-contact three-dimensional inspection of a surface-mount component prior to placement on a printed circuit board. Specifically, an arrangement to ensure acceptable alignment (i.e. co-planarity) of all component leads in the XZ or YZ plane, where XY is the plane of the component. The apparatus is embodied within a conventional pick and place machine and performs critical, in-process, lead co-planarity inspection. U.S. Pat. No. 4,959,898 also has problems. The views of each of the edges including leads are not separated from one another. There is no divider and therefore there is no separation or blocking off of the view of the leads on the opposite edge of the surface mount component from being shown in a view of the nearby edge.

To overcome the problems stated above as well as other problems, there is a need for an improved machine-vision system that can view sub portions of a device under test using backlighting. There is a further need for a machine vision system that minimizes the problems associated with specular reflections off of shiny surfaces of a device under test. There is a further need for a machine vision system that can accurately measure selected portions of a device under test. There is still a further need for a device that can isolate selected portions of a device under test to assure the accuracy of measurements made on the part. In addition, there is a need for a device that uses a single camera to produce an image with all the desired views. There is also a need for a mechanical system that allows for automated, high-speed, two-dimensional inspection of objects or devices under test.

BRIEF SUMMARY OF THE INVENTION

A machine-vision system for imaging an object having at least a first side, edge or surface, and a second side, edge or surface. The system includes an imager, and an optics apparatus that images two or more views of the first side of the object and images two or more views of the second side of the object. The two or more views of the first side of the object are each from a different angle. The two or more views of the second side of the object are also each from a different angle. The object being viewed includes at least one major surface. The machine vision system also includes a divider background surface that is placed near the at least one major surface of the object. The divider background surface is placed near the major surface of the object in order to obtain separate images of features of the object on the first side of the object and features of the object on the second side of the object. In one embodiment, the divider is opaque.

Another aspect of the invention includes a divider that diffuses light to backlight the features on the object on the first side and backlight the features on the second side of the object. In another embodiment, the divider background surface at or near a major surface of the object in order to obtain separate images of features of the object on the first side of the object and features of the object on the second side of the object. The divider diffuses light to backlight the features of the object on the first side and back light the features on the second side of the object. In some embodiments, the divider includes an elastomeric material. The system optionally also includes a base, and a spring positioned between the divider and base. The spring biases the divider toward the object when at least a portion of the divider contacts the object. The divider includes an edge for contacting the major surface of the object. In some embodiments, the edge of the divider initially forms an angle with respect to the major surface of the object. The divider is biased so that the edge of the divider is substantially in contact with the major surface of the object after initially forming an angle with the major surface of the object. The object is moved both perpendicular to and parallel to the major surface of the object between an initial position and a final position. A picker is used to pick and move objects. On the imager the views of the first side and the second side are within a single image. The machine-vision system also includes a device for measuring dimensions associated with the top view or bottom view (also called the top-down view) of the object. One of the views of the first side and the second side are within a single image on the imager. In one embodiment, a single top-down view of the object shows both the first side and the second side of the object.

Also disclosed is a machine-vision system for inspecting an object. The object has at least a first side and a second side. The machine-vision system includes an imager, and an optics apparatus that images a top down view of the object that includes both the first side and the second side of the object, a separate view of the first side of the object, and a separate view of the second side of the object. In one embodiment, the optics apparatus includes a single camera. The object also includes at least one major surface. The machine vision system further includes a divider background surface placed near or against the at least one major surface of the object. The divider background surface allows the machine vision system to obtain the separate image of the first side of the object and the separate image of the second side of the object. The optics apparatus of the machine vision system further includes a first reflective surface for obtaining the separate view of the first side of the object, and a second reflective surface for obtaining the separate view of the second side of the object. The machine-vision system also includes a base, at least one spring attaching the divider to the base, and a picker for picking and moving objects. The picker moves the object at an angle with respect to an edge of the divider. In one embodiment, a single image includes the top-down view of the object that includes both the first side and the second side of the object, the separate view of the first side of the object, and the separate view of the second side of the object, each of which is backlit. In some embodiments, the machine-vision system includes a measurement apparatus (e.g., a machine-vision computer having image analysis software) for determining dimensions on at least one of the top down view of the object that includes both the first side and the second side of the object, the separate view of the first side of the object, and the separate view of the second side of the object.

Advantageously, the machine-vision system of the present invention can view a device under test using backlighting to minimize or substantially eliminate the problems associated with gathering useful data from images having specular reflections. The machine vision system of the present invention can accurately measure selected portions of a device under test. In addition, the machine vision system of the present invention isolates selected portions of a device under test to assure the accuracy of measurements made on the part. Yet another advantage is that one camera produces an image with all the desired views, including side views of the device under test for checking the co-planarity and a top-down view for checking that the geometry of the device under test will fit a corresponding set of pads on a circuit board. The machine vision system allows automated, high-speed, two-dimensional inspection of objects or devices under test.

DETAILED DESCRIPTION OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Machine-vision and optical-feature-recognition techniques are used in some embodiments, to distinguish parts that deviate from a predetermined intended aspect of an ideal device. In this description, a "device" is meant to be any device of manufacture or object, for example an integrated circuit package, electronic part, semiconductor, molded plastic part, aluminum wheel, gemstone or even an egg or strawberry, which can be inspected. Typically, according to the present invention, a manufacturing operation will use two-dimensional and three-dimensional information acquired from inspection of the device to distinguish "good" parts from "bad" parts, and can discard the bad parts and insert previously inspected good parts in their place.

System Overview

Figure 1:
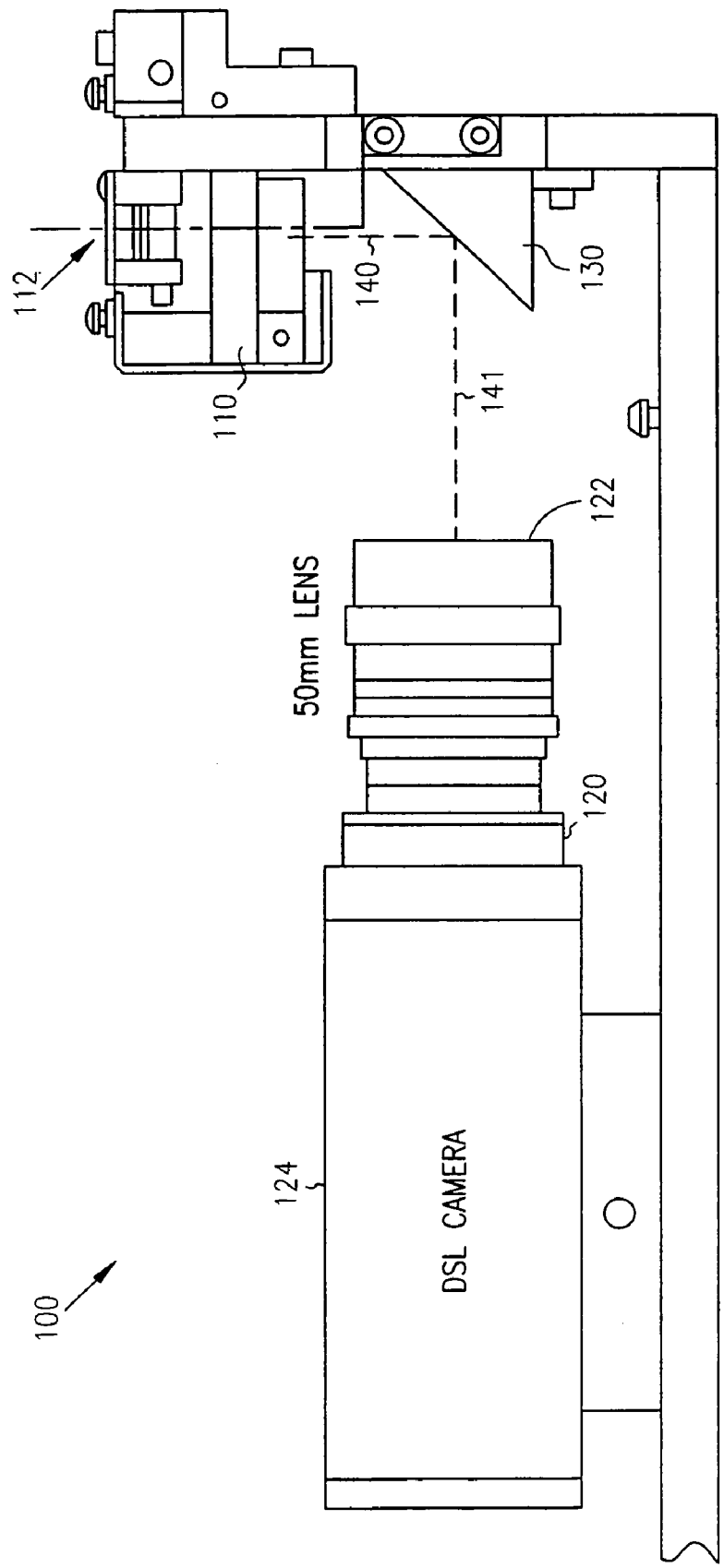
FIG. 1 is a side view of a machine vision system 100 for the inspection of devices under test which includes an embodiment of the present invention.

FIG. 1 is a side view of a machine-vision system 100 for inspection of devices under test or objects. The machine-vision system 100 includes an embodiment of the present system. Machine-vision system 100 may be used independently as an inspection station for sorting manufactured parts or may be used as part of a manufacturing line to inspect parts to be placed within an electrical component. Machine-vision system 100 includes housing 110. Housing 110 includes a portion for receiving the part or object or device under test 112. Also included within the housing are a set of optics and lights which are used to backlight portions of the part placed in the part placement area 112. The machine-vision system also includes an imaging device 120 which includes a lens 122 and an imager 124. In this particular case, the imager device 120 is a DSL camera (i.e., a video camera, having a 50 mm lens, connected to a machine-vision computer using a digital serial link wire such as described in U.S. Pat. No. 6,084,631 entitled "High-Speed Digital Video Serial Link" issued Jul. 4, 2000, incorporated herein by reference). The lens 122, as shown in FIG. 1, is placed so that the external face is in a substantially vertical orientation (i.e., with the optical axis of the lens, corresponding to light path 141, in a horizontal orientation). When the lens 122 is in a substantially vertical orientation, many problems are eliminated with respect to dust or other debris falling upon the lens and corrupting the results or corrupting the image received at the imager 124. In this particular embodiment of the machine-vision system 100, a 45° mirror 130 converts light path 140 from a vertical orientation to a light path 141 having a horizontal orientation or substantially horizontal orientation as it passes into the imager device 120. As mentioned above, the housing 110 includes a set of optics and a set of lights, typically light-emitting diodes ("LEDs") that are used to obtain an image of a certain portion of a part. The specific optics and lights of various embodiments will be discussed in more detail in FIGS. 2–4 and 6–8 and 10–14, which are further discussed below.

Figure 2:
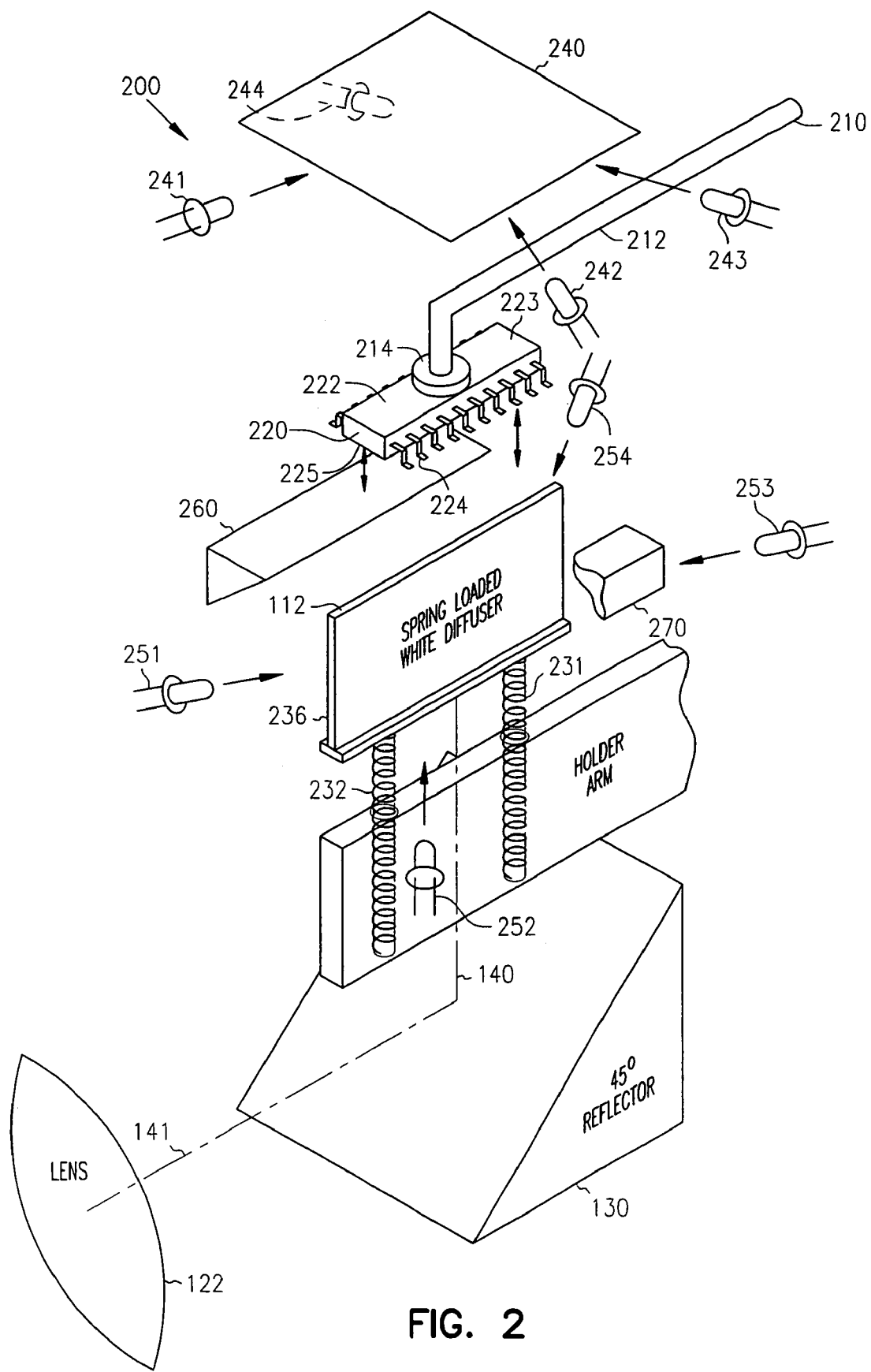
FIG. 2 is an exploded view of a first embodiment of the present invention.

FIG. 2 is an exploded view of a first embodiment of the present invention. FIG. 2 includes a lens 122 of the image device 120 as well as the 45° reflector or mirror 130 which converts a light path 140 from a substantially vertical orientation to a light path 141 having a substantially horizontal orientation and directed toward the lens 122 of the image device (shown in FIG. 1). The machine-vision system 200 shown in FIG. 2 includes a vacuum pick-and-place machine 210 which includes a vacuum line 212 and a vacuum pickup end 214. The vacuum pick-and-place apparatus 210 picks up objects 220 or devices under test 220 which are to be inspected. As shown in FIG. 2, the object 200 or device under test 220 is a surface-mount technology package having a substrate 222 and gull-wing type leads 224. The gull-wing shaped leads 224 are on a first side or edge and a second side or edge of the substrate 222. In other embodiments, the device under test includes solder balls affixed to the bottom surface, some of which are blocked from view by placing backlit diffuser 230 between rows of balls, allowing inspection of the balls in front of (towards the imager camera relative to) the diffuser 230. The substrate 222 also has a first major surface 223 and a second major surface 225. The vacuum pick-and-place assembly 210 places the object or device under test 220 at the inspection site 112 which is essentially above or in contact with a spring-loaded diffuser 230. In some embodiments, the diffuser 230 is spring loaded on a first spring 231 and a second spring 232. The springs 231 and 232 are attached to a holder arm 234. The area for the parts (inspection site) 112 is atop or near the edge 236 of the spring-loaded diffuser 230. When properly placed, the vacuum pick-and-place assembly 210 places the object or device under test 220 and specifically the second major surface 225 in contact with the edge 236 of the spring-loaded diffuser 230. When properly placed, the edge 236 of the spring-loaded diffuser 230 is placed between the two rows or sets of gull-wing leads 224 on the object or device under test 220. The machine-vision system includes the first diffuser 230 as well as a second diffuser 240. The second diffuser 240 is placed above the first major surface 223 of the device under test or object 220. The second diffuser 240 is a translucent material backlit from above with a series of one or more (in this embodiment, four) light-emitting diodes directed at the surface of the diffuser which is behind the first major surface 223 of the object or device under test 220. In other embodiments, diffuser 240 is opaque, with a matte surface, and is illuminated by LEDs from below. Each of the LEDs 241, 242, 243, 244 are directed toward the surface of the diffuser 240 which is between the main portion of the diffuser and the device under test or object 220. Another set of LEDs 251, 252, 253, 254 are directed at the diffuser 230 which contacts the second major surface 225 of the object under test when properly positioned.

It should be noted that in one embodiment, each of the LEDs 241, 242, 243, 244, 251, 252, 253, 254 remain on, or are pulsed simultaneously to an on state, so that all the views of the part which are desired are acquired simultaneously by the imaging device 120. In another embodiment, sets of the LEDs may be pulsed at different times to acquire images of specific parts of the device under test or object 220 so that separate images may be acquired. The advantage of the first embodiment of LEDs is that all of the images are acquired simultaneously at the imager 120 (shown in FIG. 1). The advantage of the second embodiment of LEDs where they are pulsed at various times is that the imager need not be as large. The disadvantage of the second embodiment is that pulsing various sets of LEDs to acquire separate images takes more time as compared to acquiring all the images simultaneously or substantially simultaneously.

Also included in the first embodiment of the machine-vision system is a left-side mirror 260 and a right-side mirror 270. The left-side mirror is oriented at a 45-degree angle for acquiring a backlit image of a first side or edge of the device under test. The right-side mirror 270 is for acquiring a separate image of the other side of the device under test 220. The spring-loaded diffuser 230 is placed near or touching the second major surface 225 of the device under test or object 220, to assure that the pins imaged by the left-side mirror 260 are separated from (not blocked by views of) the pins imaged by the right-side mirror 270. Thus, the left-side mirror 260 acquires an image of the left-side of the device under test 220. With diffuser 230 blocking any view of the pins on the other side. And the right-side mirror 270 obtains a separate image of the right-side of the part or object or device under test 220. The light path from the left-side of the part 220 is directed by mirror 260 toward the 45° reflector 130 and into the lens 122 of the imaging device 120 (shown in FIG. 1) while the right-side mirror 270 directs a light path to the 45° reflector 130 and into the lens 122 of the imaging device 120. In some embodiments, the central field of reflector 130 obtains a backlit outline of both sides of part 220. The 45° reflector 130 includes a light path 140 of this view and converts the light path to a horizontal light path 141 which is directed toward the lens 122 of the imaging device 120 (shown in FIG. 1). In each instance, the various views are backlit by the various LEDs. This minimizes or reduces the incidence of specular reflections in the views received by the imaging device. In some embodiments, the 45° reflector also obtains a front-lit view of the second major surface 225 (i.e., the bottom surface of the part 220).

Figure 3A:
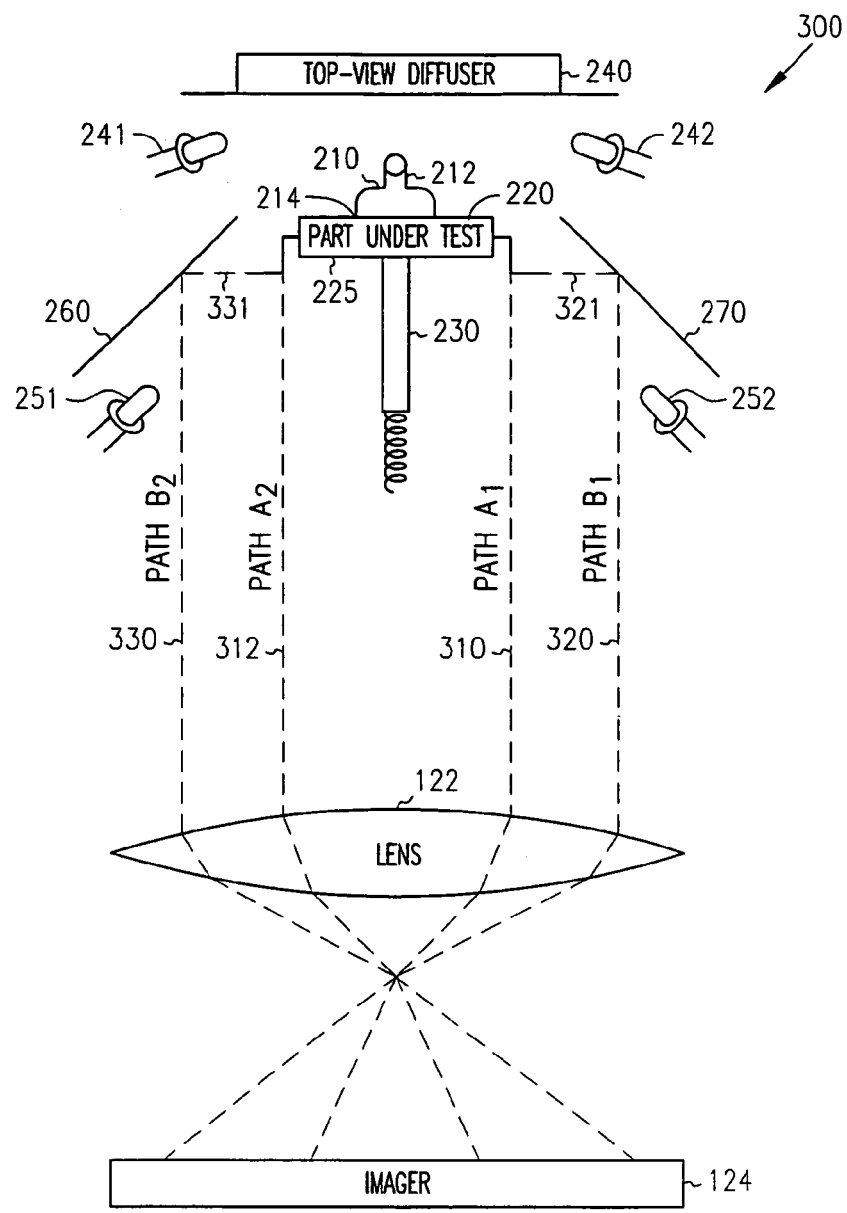
FIG. 3A is a schematic view of a second embodiment of the present invention.
Figure 3B:
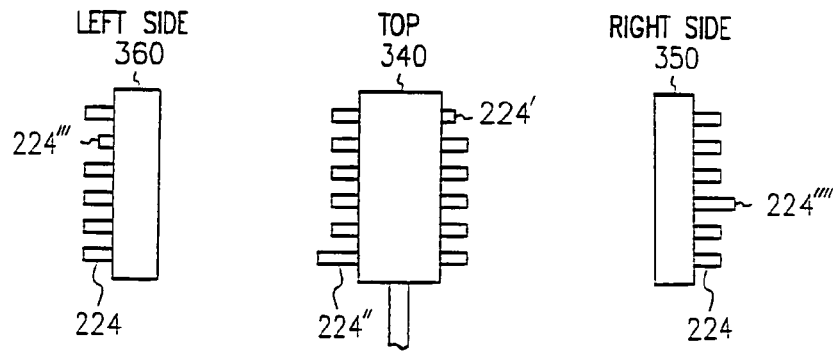
FIG. 3B is a representation of the view received at the imager.

FIG. 3 shows a second embodiment of the machine-vision system 300. The second embodiment of the machine-vision system 300 differs only slightly from the first embodiment of the machine-vision system 200. In the second embodiment 300, the 45° reflector or mirror 130 (shown in FIGS. 1 and 2) has been eliminated. Therefore, the front surface of lens 122 is now substantially horizontal rather than vertical. In addition to the lens 122 being horizontal or substantially horizontal, the imager 124 is also horizontal rather than vertically oriented. The schematic shown in FIG. 3 shows the various paths for light to get a left-side view, a separate right-side view and a top-down view of the device under test or object 220. The light paths A1 and A2 depicted by reference numerals 310 and 312, respectively, represent the paths necessary to form the top backlit image 340 received by the imager 124. Path B1 denoted by reference numeral 320 represents the light path which produces the right-side image 350 at the imager 124. Light path 320 includes a portion 321 from the right-side mirror 270 to the tip of the gull-wing lead. The length of light path B1 is slightly longer than the length of light path A1 (by a distance shown as path length 321) between the gull-wing leads and the mirror 270. Similarly, path B2 depicted by reference numeral 330, is slightly longer than the paths A2 and A1 which carry the reference numerals 310 and 312, respectively, by an amount equal to the path segment 331 between the mirror 260 and the edge of the gull-wing leads 224 on the edge of the device under test 220. Light path B1 and light path B2 are longer than light path A1 and light path A2. In each instance, it is by a segment or a path length depicted by reference numerals 321 and 331 in FIG. 3A. Therefore, the lens 122 shown in FIG. 3A has a depth of focus which accommodates the difference in the light path lengths, A1, A2 versus the longer light path lengths B1 and B2. In other words, the depth of field or the depth of focus associated with the lens 122 allows the view produced by light paths B1 and B2 to be in focus as well as the views or top-down views produced by light path A1 and light path A2. Light paths A1 and A2 represent a forming of the top-down view of the device under test or object 220. From the top-down view 340 in FIG. 3B, determination of the length that each of the gull-wing leads 224 extends from an edge of the part can be determined. Also, the distances between the leads can be measured or determined to assure that the leads will fit onto the pattern which the device under test is to solder or be added to, to form an electronic part. For example, the top-down view 340 reveals that there is a short lead 224' and a long lead 224". Measurements can be made with respect to the length of these leads 224', 224" to see if the part or object under test 220 should be accepted or rejected. If the length of the lead 224' or the length of the lead 224" is within tolerance, then the part or device under test is accepted. If on the other hand, the lead 224' is so short that it will not make reliable electrical contact with the pattern on a circuit board (not shown), then the device under test or object 220 will be rejected and placed in a bin for either rework or scrap. Each of the separate views of the left-side 360 shown in FIG. 3B or the right-side 350 shown in FIG. 3B, are used to check the co-planarity of the leads. In other words, for a surface-mount type of object 220, it is necessary that all of the leads are substantially coplanar. As shown in image 360 in FIG. 3B, there is one lead 224''' that is substantially shorter than all the other leads 224 shown in the left-side view 360 of the image shown in FIG. 3B. In some embodiments, a computer reviews the image 360 looking for leads such as 224''' (higher) which are not coplanar or substantially coplanar with the other leads 224. Similarly on the right-side view 350, there is one lead 224'''' that is lower than all of the rest of the leads 224 and, therefore, the part may be rejected due to the problems with co-planarity. The problems with co-planarity indicate that the part or device under test, specifically the leads 224, will not allow the part 220 to lie flat on the electronic device or circuit board to which it is going to be attached. There can be problems with co-planarity when soldering leads to a printed circuit board, for example. The problems include weak solder joints or solder joints which do not connect, or may at some later time become disconnected and, therefore, result in failure of a device formed from a device or object under test 220. It should be noted that the imaging device 120 also includes or is connected to a microprocessor or computer which flips the image seen at the imager 124 before displaying simultaneously the images 340, 350, 360 as shown.

Figure 4A:
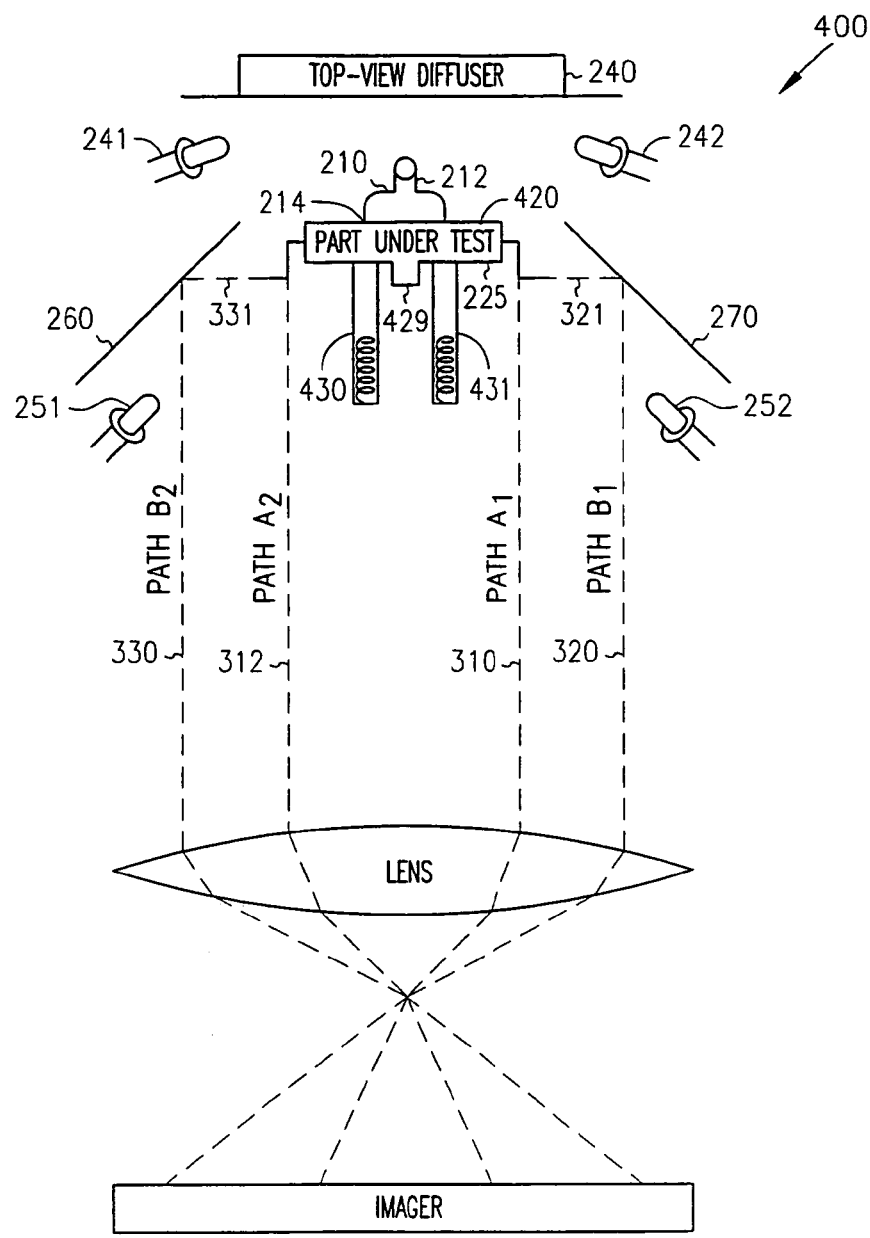
FIG. 4A is a schematic view of a third embodiment of the present invention in which the diffuser positioned near a major surface of the device under test is double walled.
Figure 4B:
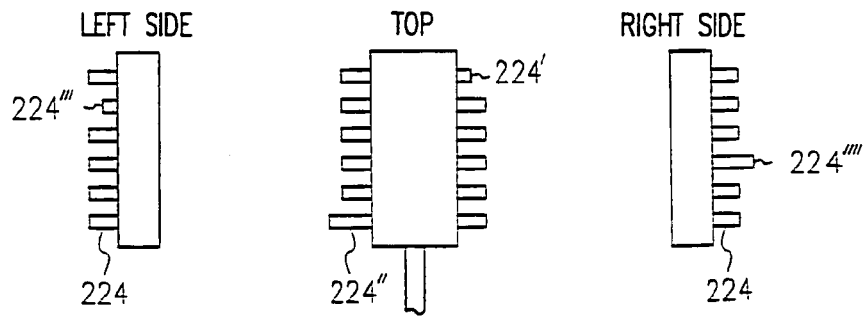
FIG. 4B is a representation of the view received at the imager.

FIG. 4A is a schematic view of a third embodiment of the present invention in which the diffuser is positioned near the major surface of the device under test 220. The embodiment 400 shown in FIGS. 4A and 4B differs only slightly from the embodiment 300 shown in FIGS. 3A and 3B, in that two diffusers 430 and 431 are used to, for example, block a part feature 429 that extends downward from the lower major surface 225 (i.e., placing one diffuser on each of both sides). The images received at the imager and processed by a computer as depicted in 4B, are precisely the same as the images obtained in the embodiment shown in FIG. 3A and the images of which are displayed in FIG. 3B. For the sake of brevity, rather than describing the entire embodiment 400, the major differences will be discussed with the understanding that the rest of the arrangement stays substantially the same. One major difference is that there is a first diffuser 430 and a second diffuser 431 that replace the single diffuser 230 shown in FIG. 3A. In other words, a double-walled or pair of diffusers 430, 431 replace a single diffuser. The pair of diffusers 430 and 431 separate the right-side view from the left-side view and also block centrally located features of part 420 such as protrusion 429 (for example, pre-applied pressure-sensitive adhesive used to temporarily attach to a circuit board until soldered).

Diffuser 430 is lit or illuminated or backlit by LED 251 and 254 (shown in FIG. 2). The diffuser 431 is backlit or illuminated by LED 252 and LED 253 (shown in FIG. 2). The paths for obtaining the separate side view, path B2 carrying the reference number 330 and path B1 carrying the reference number 320, are exactly the same as shown in FIG. 3A. The top-down view which is obtained or acquired by light paths A1 and A2 carrying the reference numerals 310 and 312, respectively, is also the same. Therefore, the only difference is that a pair of side view diffusers 430 and 431 now replace the single diffuser shown in FIG. 3A. It should be noted that in another embodiment, an LED or other light source is placed between the two diffusers 430, 431. In this embodiment, the LEDs 251, 252, 253 and 254 which are directed at these diffusers 430, 431 may be eliminated. The positioning of a light source between the two diffusers 430, 431 further reduces any possible specular reflections that are otherwise produced by directing the light source toward the diffusers 430, 431.

However, in some embodiments, front-lit illumination and back-lit illumination are both provided (either simultaneously or alternating in time) to obtain further information about the object under test. For example, in some embodiments, the back-lit illumination is provided by simultaneously strobing LEDs projected onto the side-view diffuser 230 (e.g., LEDs 251, 252, 253, 254 obliquely projected to the matte surface of diffuser 230 of FIG. 2) and top-down examination diffuser 240 (e.g., LEDs 241, 242, 243, 244). This provides backlit images of the top-down view as well as two side views onto a single captured video image. Then, in some embodiments, a separate set of LEDs (not shown) directed to provide front-lit illumination onto both sides of part 220 as well as the bottom surface and leads of part 220 is strobed while LEDs 251, 252, 253, 254 and LEDs 241, 242, 243, 244 are kept off. This provides front-lit images of the bottom-up view as well as two side views onto a single captured video image.

Figure 5A:
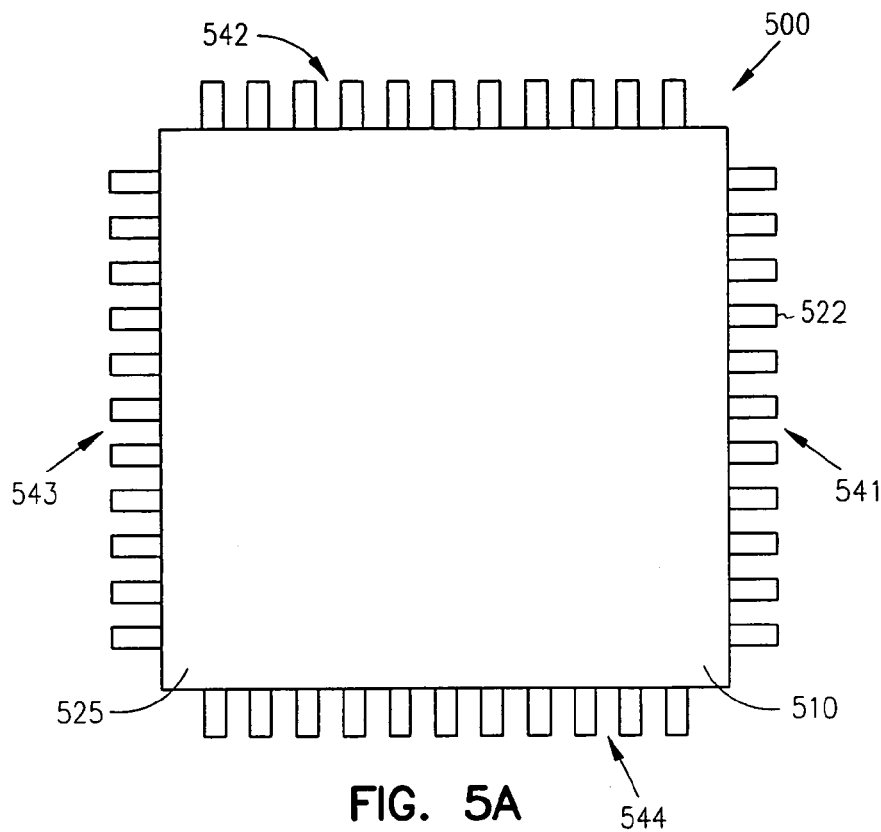
FIG. 5A is a bottom view of a quad flat pack package.
Figure 5B:
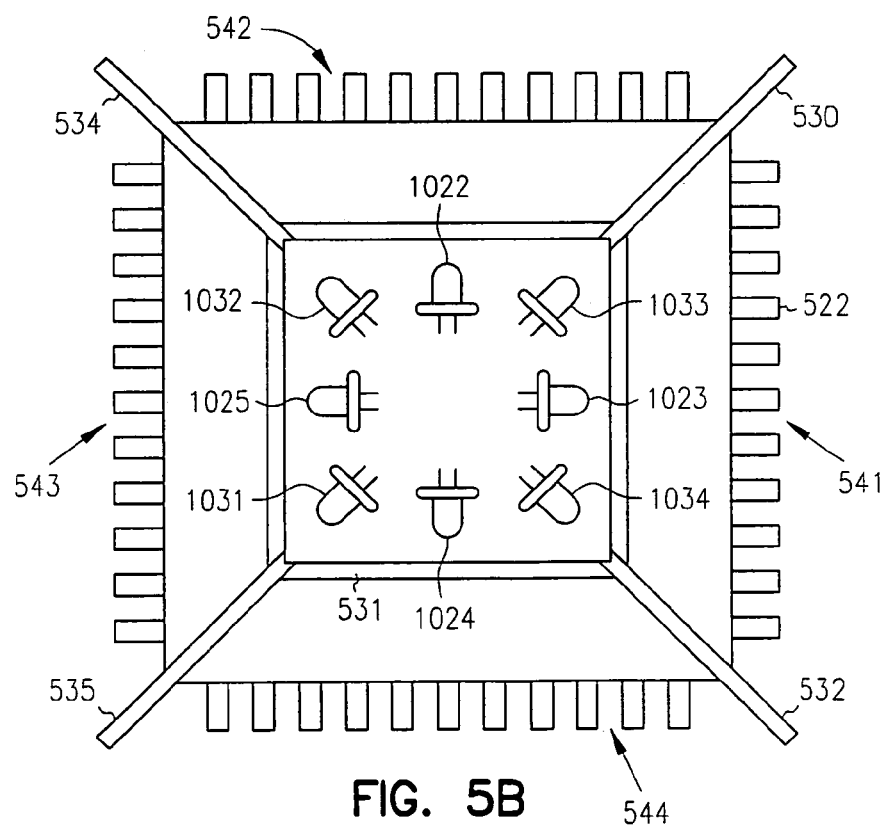
FIG. 5B is a bottom view of a quad flat pack package with a diffuser that isolates the features at each of the edges.

Now turning to FIGS. 5A and 5B, another embodiment of the diffuser as well as the machine vision system will be discussed. FIG. 5A is a bottom view of a quad flat pack package and FIG. 5B is a bottom view of a quad flat pack package with a diffuser 530 that isolates the features on each of the four edges of the quad flat pack. Quad flat pack package 500 includes a substrate 510 having a first major surface 525 and an opposite-facing second major surface (not shown). The quad flat pack package 510 includes four edges 541, 542, 543 and 544. Each of the edges 541, 542, 543, 544 carries a row of leads 522. The invention allows each of the edges 541, 542, 543, 544 of the quad flat pack package 500 to be isolated and backlit in three (if the top-down view of both sides is considered a single view) or four separate views. As shown in FIG. 5B, one embodiment of diffuser 530 has a substantially rectangular or square inner diffuser core 531 and several diffuser wings 532, 533, 534, 535. Each of the wings 532, 533, 534, 535 bisects a corner of the quad flat pack package 500. In other words, wings 532 and 533, as well as the box-like center portion 531 of the diffuser 530 isolate the edge 541 from the other edges 542, 543, 544 of the quad flat pack package. Similarly, wings 533, 534, as well as the inner core 531, isolate edge 542 from the other edges of the quad flat pack package 500. Wings 534 and 535, as well as the inner core wall 531 of the diffuser 530 isolate side or edge 543 of the quad flat pack package from the other edges 544, 541, 542. In addition, wings 532 and 535, as well as the core portion 531 of the diffuser 530, isolate edge 544 from the other edges 541, 542, 543. For the purposes of inspection, a top-down image, as well as two sides, can be acquired in a first position and then the quad flat pack package can be turned 90° so that the other two edges and a top-down view can be obtained. In another embodiment, a machine-vision device is provided with not only a left-side mirror and a right-side mirror but a front and a back mirror so that each of the edges 541, 542, 543, 544 can be viewed and sent to a lens 122 and to an imager 124. The end result would be an isolated view of each edge 541, 542, 543, 544, as well as a top-down view of the quad flat pack package 500 simultaneously obtained to a single captured image field. LEDs would be used to back light the various quadrants formed by the diffuser 530, as well as a top diffuser such as that shown in FIGS. 2, 3A and 4A. It should be noted that the inner core portion 531 of the diffuser 530 can be made larger or smaller. In some embodiments, there may not be an inner core portion and there would be four wings on diagonals that would separate the various edges 541, 542, 543, and 544 from one another.

In some embodiments, diffuser 530 is made of translucent material (such as milky plastic) and LEDs on the interior provide illumination. For example, LEDs 1031–1034 provide edge-input illumination to wings 532–535, and LEDs 1022–1025 provide back light illumination onto walls of box 531.

In some embodiments of each of the embodiments described herein, multiple cameras are used in place of the single camera shown.

Figure 6A:
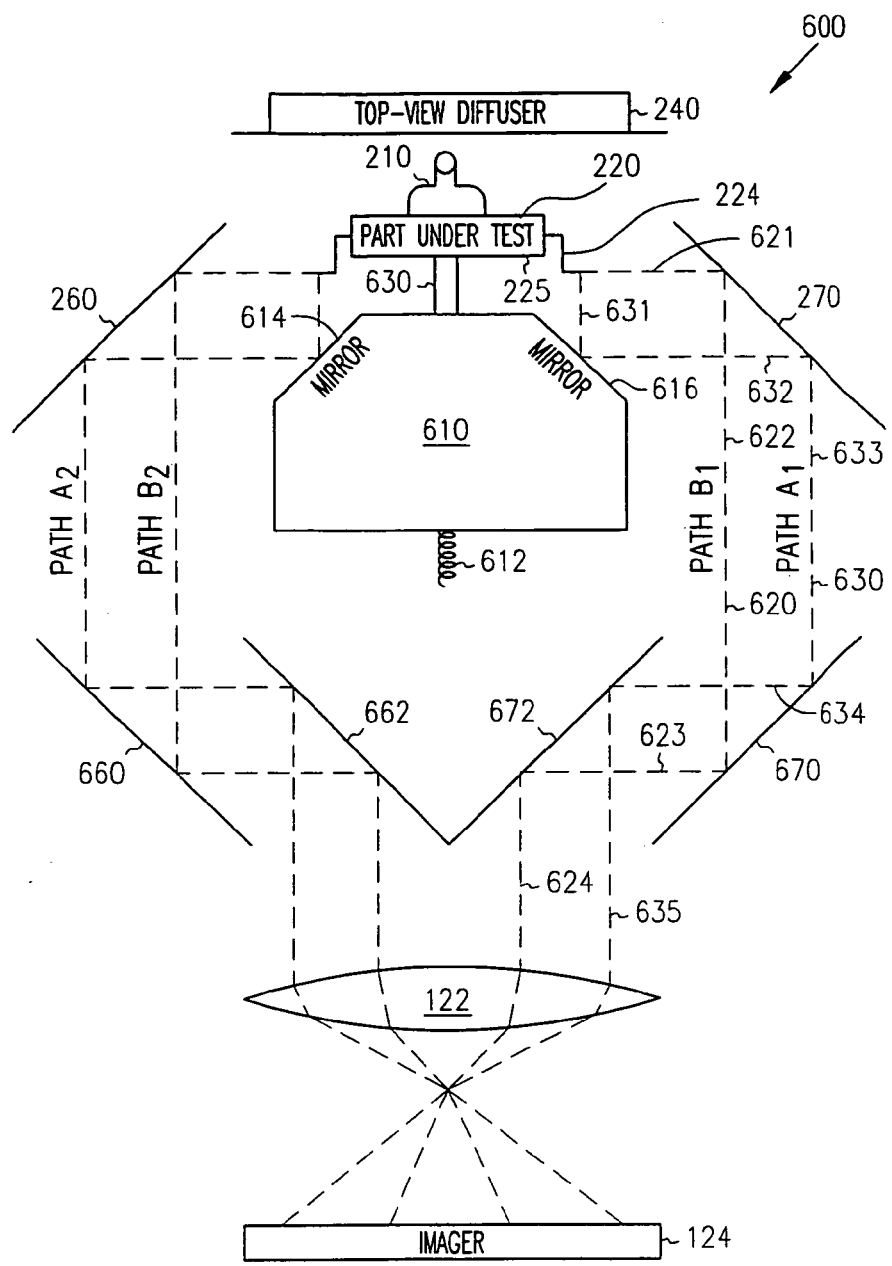
FIG. 6A is a schematic view of a fourth embodiment of the present invention in which the diffuser is positioned above the device under test and a series of mirrors produces at least two separate images of at least two edges of the device under test.
Figure 6B:
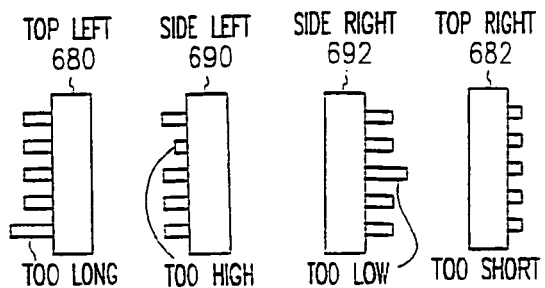
FIG. 6B is a representation of the view received at the imager.

FIG. 6A is a schematic view of another embodiment of the present invention 600 in which one diffuser 240 is positioned above the device under test 220. A pick-and-place assembly 210 places a part under test or device under test 220 onto a base 610. The base includes a diffuser 630 attached a portion of the base 610 which is closest to the second major surface 225 of the device under test 220. The base 610 also includes a first 45° mirrored or reflective surface 614 and a second mirrored or reflective surface 616 which is also at 45°. Light is directed at the top-down view diffuser 240 as well as at the diffuser 630. In one embodiment, the LEDs are used as light sources to back light the diffuser 630 in the top-down view diffuser 240. Also included in the machine-vision system 600 is a left-side mirror 260 and a right-side mirror 270. In addition to the left-side mirror 260, there is a first lower side mirror 660 and a second lower side mirror 662. Both of these mirrors 660, 662 are at 45°. In addition to the right-side mirror 270, there is a first lower right-side mirror 670 and a second lower right-side mirror 672. Both of these mirrors 670, 672 are also at 45° angles. It should be noted that all of the mirrors 614, 616, 660, 662, 670, 672 and 260, 270 do not necessarily have to be mirrors per se but may present reflective surfaces. The embodiment 600 and the arrangement of mirrors 260, 270, 614, 616, 660, 662, 670, 672 are used to produce separate images as shown in FIG. 6B. The separate images include a top left-side 680, a top right-side 682, a left-side view 690 and a right-side view 692. The top left-side 680 and the top right-side 682 are used to determine the footprint dimensions of the device under test 220. The left-side view 690 and the right-side view 692 are used to check the leads 224 for co-planarity. Each of the views formed are separate from one another and each of the views formed are backlit so that specular reflections are either eliminated or minimized. Light path A1 is used in formulating or acquiring the top right image 682 shown in FIG. 6B. Light path A1 carrying the reference numeral 630 includes light path segments 631 from the right-side edge of the lead 224 to the mirror 616 and light path segment 632 from the mirror 616 to the right-side mirror 270 and light path segment 633 from the right-side mirror 270 to the first right-side lower mirror 670 and light path segment 634 from the first lower right-side mirror 670 to the second right-side mirror 672 and light path segment 635 from the second lower right-side mirror to the lens 122. Light path A2 is similar to light path A1 except that it uses the left-side mirrors 614, 260, 660, 662. Light path A2 enters the lens 122 as does light path A1. Both these light paths go to the imager 124 of the imaging device 120 (shown in FIG. 1). Light path B1 and light path B2 are also symmetrical. As opposed to describing both, only light path B1 will be described. Light path B1 results in the right-side view 692 shown in FIG. 6B. Light path B1 which carries the reference numeral 620 includes light path segments 621 from the lead 224 to the right-side mirror 270, light path segment 622 from the right-side mirror 270 to the lower right-side mirror 670, light path segment 623 from the first lower mirror 670 to the second lower mirror 672, and light path segment 624 from the mirror 672 to the lens 122.

It should be noted that, in some embodiments (not shown), path A1 and path B1 are made equal in length so that the lens 122 does not have to accommodate different focal points.

An additional advantage of the embodiment 600 shown is that the mirrors 616, 670, 672 and the mirrors 260, 614, 660 and 662 route the light paths around the base 610. It should be noted that path A results in the top right-side view 682 shown in FIG. 6B. Path B1 produces or results in a right-side view 692 shown in FIG. 6B. Path B2 produces the top-down view of the left-side of the device under test, also referred by reference numeral 680 in FIG. 6B. Path B2 results in a left-side view of the device under test 220. The side views 690 and 692 are used to determine the co-planarity of the various leads 224 on the device under test, while the top left view 680 and the top right view 682 are used to determine whether or not the footprint of the device under test will match the pattern for soldering purposes on a circuit board (not shown).

Figure 7A:
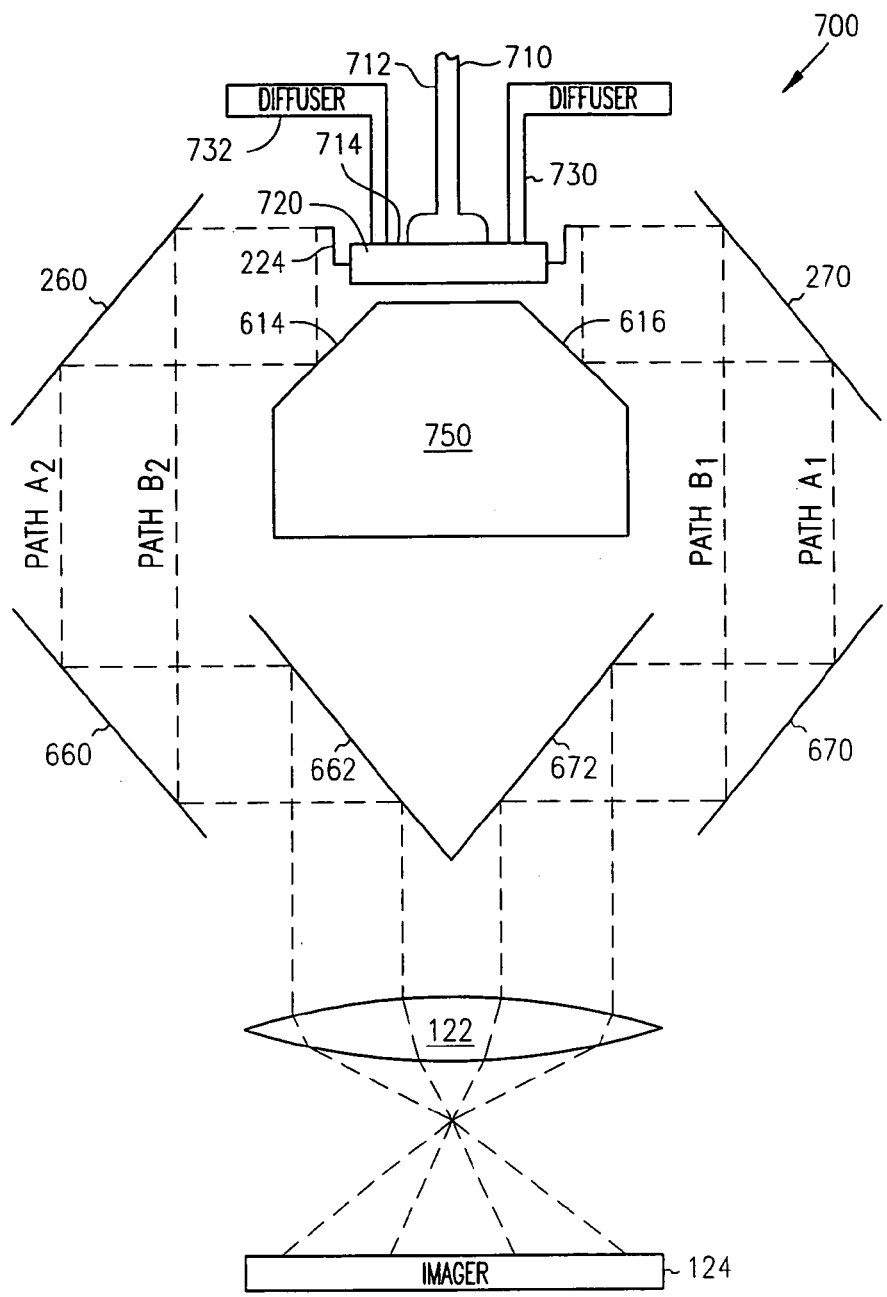
FIG. 7A is a schematic view of a fifth embodiment of the present invention in which the picker mechanism includes a set of side and top diffusers positioned above the device under test and in which a series of mirrors produces at least two separate images of at least two edges of the device under test using a dead bug orientation.
Figure 7B:
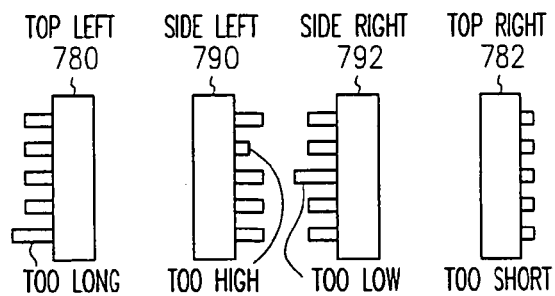
FIG. 7B is a representation of the view received at the imager.

FIGS. 7A and 7B show another embodiment of machine-vision system 700. This particular embodiment of machine-vision system 700 is very similar to the embodiment of the machine-vision system 600 shown in FIGS. 6A and 6B. The machine-vision system of the embodiment 700 differs from embodiment 600 of the machine-vision system in that the object or device under test is flipped over. If the device under test 220 is a surface-mount electronic package, this is commonly referred to as carrying the device in a dead-bug position. The main difference between the embodiment 700 and the embodiment 600, shown in FIGS. 6A and 6B, is that the pick-and-place device 710 not only includes a vacuum line 712 and a vacuum head 714 but also includes a first L-shaped diffuser 730 and a second L-shaped diffuser 732. Each L-shaped diffuser 730, 732 replaces the top-down view diffuser 240 and the diffuser attached to the base 630. As a result, there is no need for a separate top-down view diffuser 240 and side-view diffuser 630 attached to the base. LEDs are used to back light the part and illuminate the diffusers 730, 732. The images obtained in FIG. 7B will be substantially the same as those shown in FIG. 6B, although they will be obtained while the part or device under test is in a dead-bug position. The images obtained will be two top-down views of the left side 780, and right side 782 and a left-side view 790 and a right-side view 792. The side views 790, 792 are used to check the co-planarity while the top-down views of the right and left sides 780, 782 are used to determine if the footprint of the part will match the placement of the part onto pads on a printed circuit board or the like.

In some embodiments, the L-shaped diffuser 732, 731 is backlit and can be used for both the top-down views 780, 782 and the side views 790, 792. The embodiment 700, shown in FIG. 7A, includes a base 750. The base 750 includes mirrored surfaces 614 and 616. The device under test 220 does not have to contact a portion of the base and, therefore, the base 750 does not have to be spring loaded. In some embodiments, the base may be extended to include the mirrors 662 and 672. With respect to the light paths needed to obtain all four of the images 780, 782, 790, 792, the light paths are essentially the same as those shown and described in FIG. 6A with the exception that the gull-wing leads shown are on a part that is in the dead-bug position. Each of the paths A1, A2, B1, B2 are equal in length so that the lens 122 need not accommodate different focal lengths. The light path A1 is essentially the same in FIG. 7A as in FIG. 7B and the light path B1 is essentially the same in FIG. 7A as in 7B, therefore, these light paths will not be described for the sake of brevity.

Figure 8A:
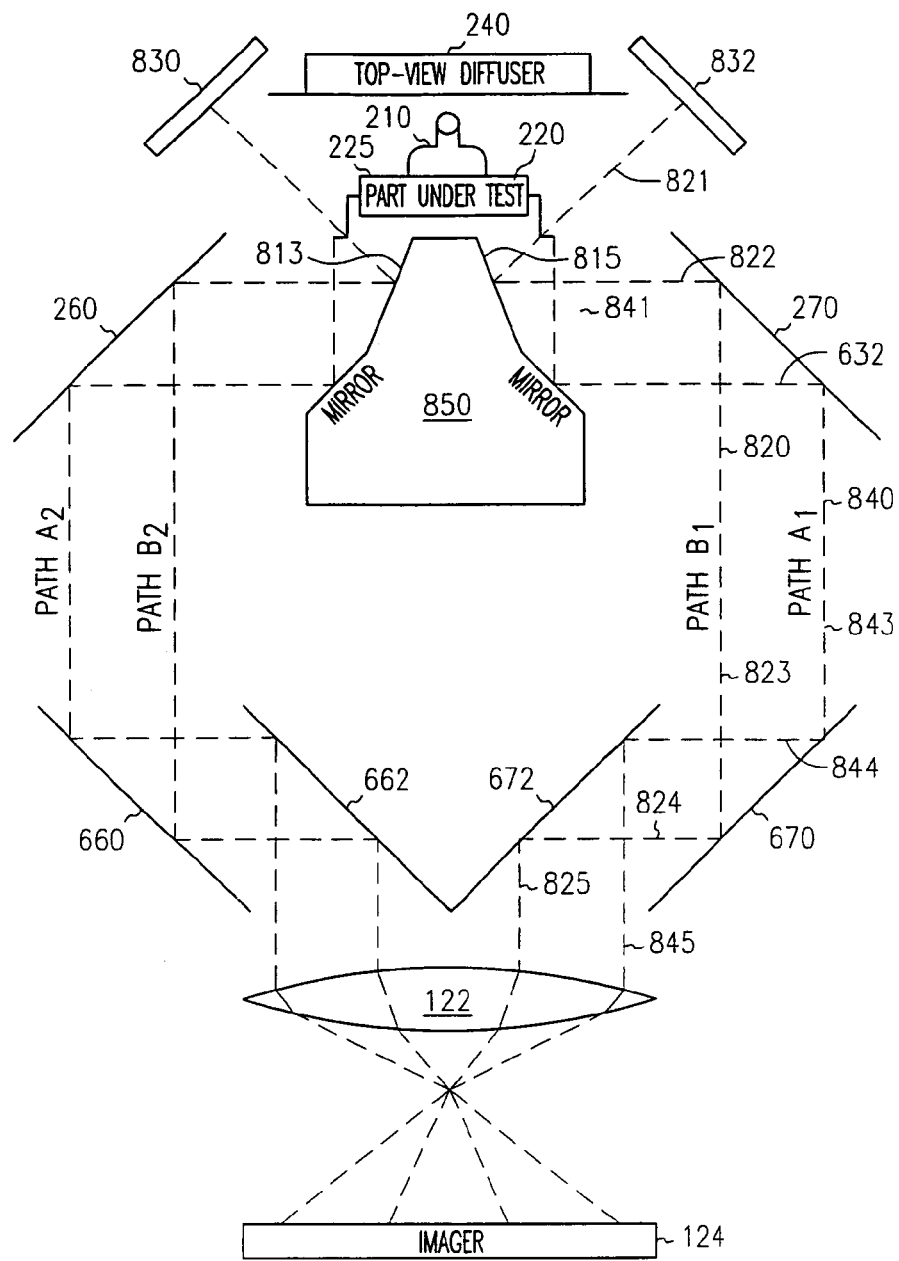
FIG. 8A is a schematic view of a sixth embodiment of the present invention.
Figure 8B:
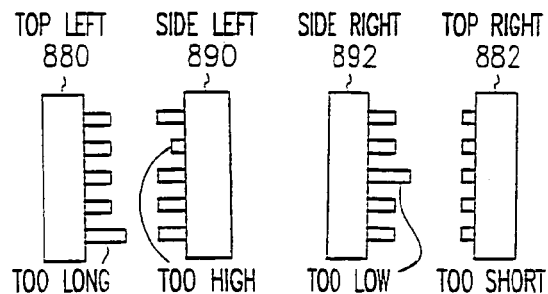
FIG. 8B is a representation of the view received at the imager.

FIG. 8 shows another embodiment of the machine-vision system 800. In this particular embodiment, there is included a base 850 which has a pair of 45° mirrors 614, 616 and a pair of 22½° mirrors 813, 815. The top-down view diffuser is in a plane that is substantially parallel to the major surfaces 223, 225 of the device under test 220. The diffusers 830 and 832 are positioned at roughly 45° with respect to the major planes 223, 225 of the device under test. The images obtained by paths A1 and A2 are top-down back-lit images of the right-side and the left-side of the device under test 220. Path A1 is very similar to the path A1 shown and described in FIGS. 7A and 6A. Path A1, which carries the reference numeral 840, includes a path segment 841 between leads 224 and the 45° mirror 616 on the right-hand side of the base 850. Path A1 also includes a segment 842 from mirror 616 to right-side mirror 270 and a path 843 from the mirror 270 to the lower right-side mirror 670 and a path segment 844 from the mirror 670 to the second lower right-hand side mirror 672. Finally, path A1 includes a segment 845 from the lower right-hand mirror 672 to the lens 122 and to the imager 124 of the imaging device. Path A1 results in the top-down view of the right-hand side, which carries the reference numeral 882 in FIG. 8B. Path A2 is symmetrical to the path A1 and uses the left-hand mirror 614, 260, 660, 662 to produce a light path between the leads 224 on the left-hand side of the device under test 220 to the lens 122 and imager 124. Light path A2 produces a top-down view of the left-hand side of the part, which carries the reference numeral 880, in FIG. 8B. The light path B1, which carries the reference numeral 820, includes a light segment 821 from leads 224 on the right-hand side of the part to the 22½° mirror 815 on the right-hand side of the part. Light path B1 also includes a light path segment 822 from the mirror 815 to the right-hand side mirror 270. Light path segment B1 also includes segment 823 from the right-side mirror 270 to the lower right-side mirror 670. Light path B1 also includes segment 824 from the lower right-hand mirror 670 to the second lower right-hand mirrored surface 672. Finally, light path B1 includes a light path segment 825 from the lower mirror 672 to the lens 122, then to the imager 124. The view represented by light path B1 is represented by reference numeral 892 in FIG. 8B. The view is up and to the right-side of the right-side of the device under test. This is sometimes referred to as the 2½ dimension view. The upward and to the right-side view can be used to check co-planarity of the leads 224 on the right-hand side. Similarly, path B2 includes similar segments that utilize the 22½° 813 and the left-side mirrors 260, 660, 662. Light path B2 goes from mirror 662 into the lens 122 and forms an image on the imager 124 which corresponds to the up and to the side left view or 2½ D view 890, shown in FIG. 8B. It should be noted that light paths A1 and A2 are of equal lengths but the equal lengths are different than the lengths of the light paths B1 and B2. Therefore, the lens 122 used in the embodiment 800 of the machine-vision system must accommodate slight differences in focal length. Thus, system 800 provides the top-down examination back-lit view plus two back-lit views, each at 45° to the plan of the second major surface of part 220.

Figure 9:
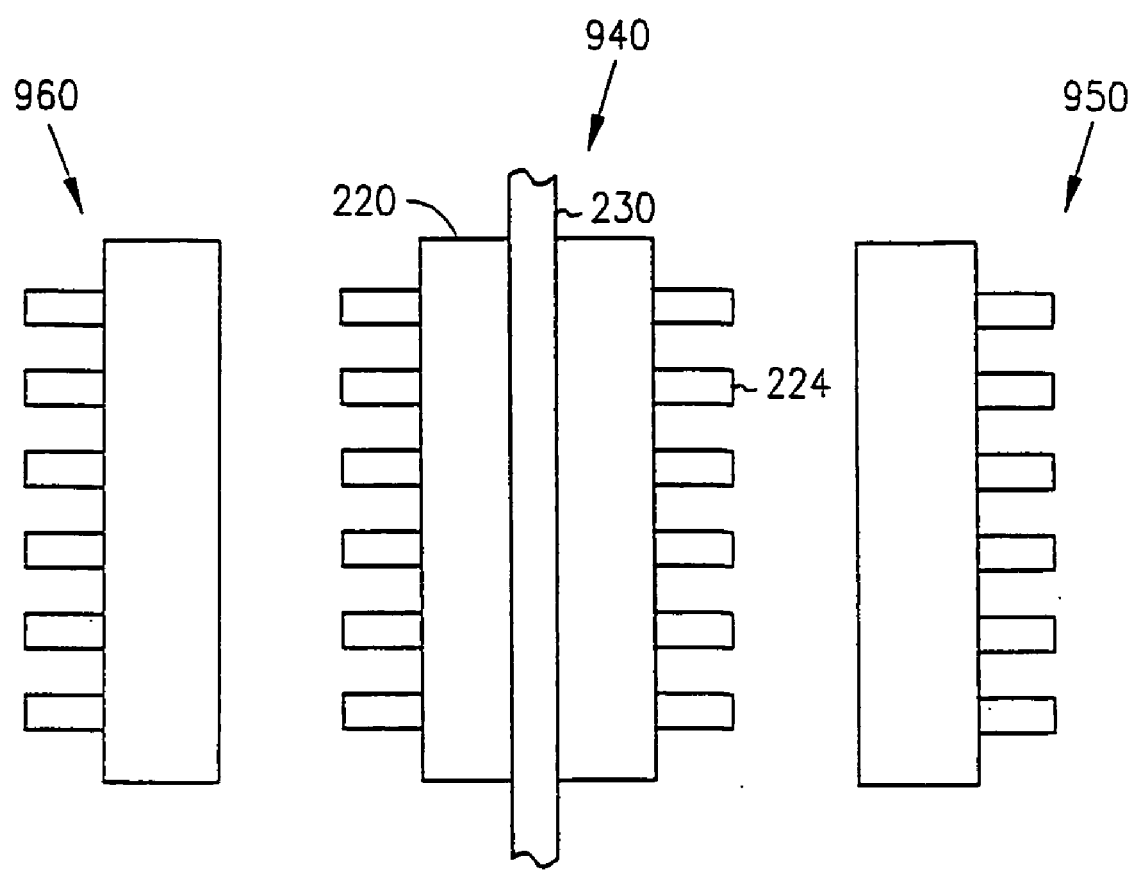
FIG. 9 is an image from an imager showing a diffuser, a top-down view and two separate side views.

FIG. 9 is an image obtained from a machine-vision system 200 shown in FIG. 2. The image 900 includes a top-down view 940, a right-side view 950 and a left-side view 960. The image also shows the diffuser 230 which splits or appears in the top side view and is positioned between the row of leads 224 on the right-hand side versus the row of leads 224 on the left-hand side of the device under test 220. As described in FIG. 2, the LEDs are used to back light a white diffuser 240. It should be noted that the bank of LEDs used to illuminate the diffuser 230 appear to have caused specular reflections in the top-down view. As discussed before, specular reflections can cause difficulty in trying to interpret the images acquired. Therefore, there is a need to minimize, or even eliminate, these specular reflections.

Figure 10A:
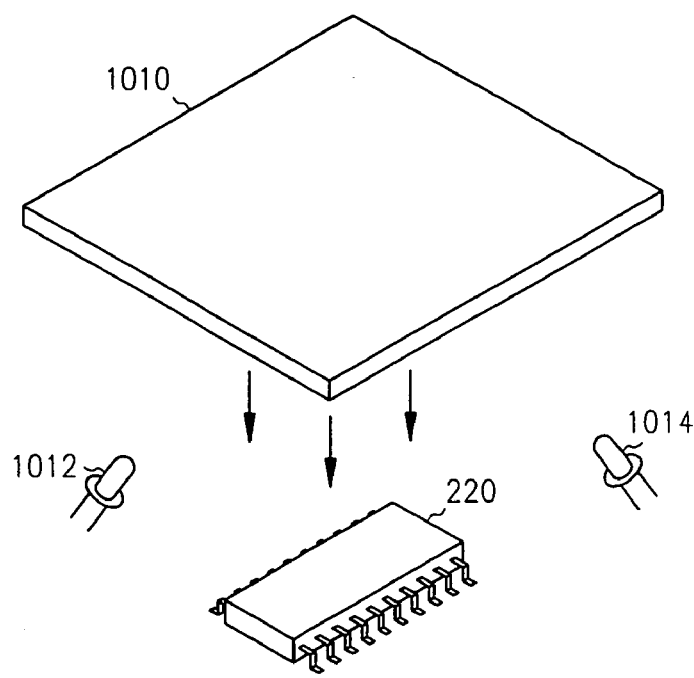
FIG. 10A is a perspective view of a first type of diffuser which can be used in the present invention.
Figure 10B:
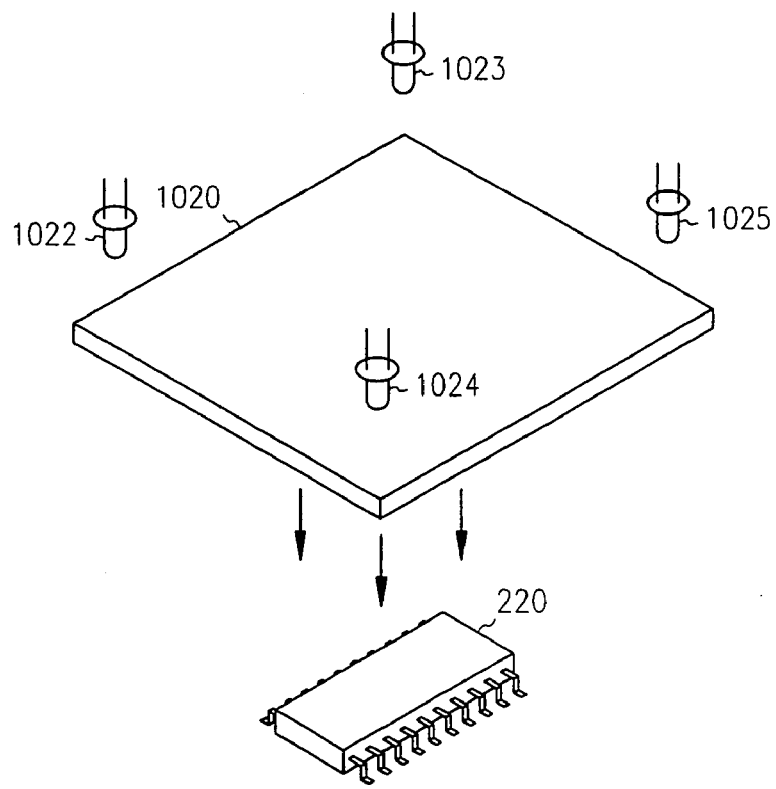
FIG. 10B is a perspective view of a second type of diffuser which can be used in the present invention.
Figure 10C:
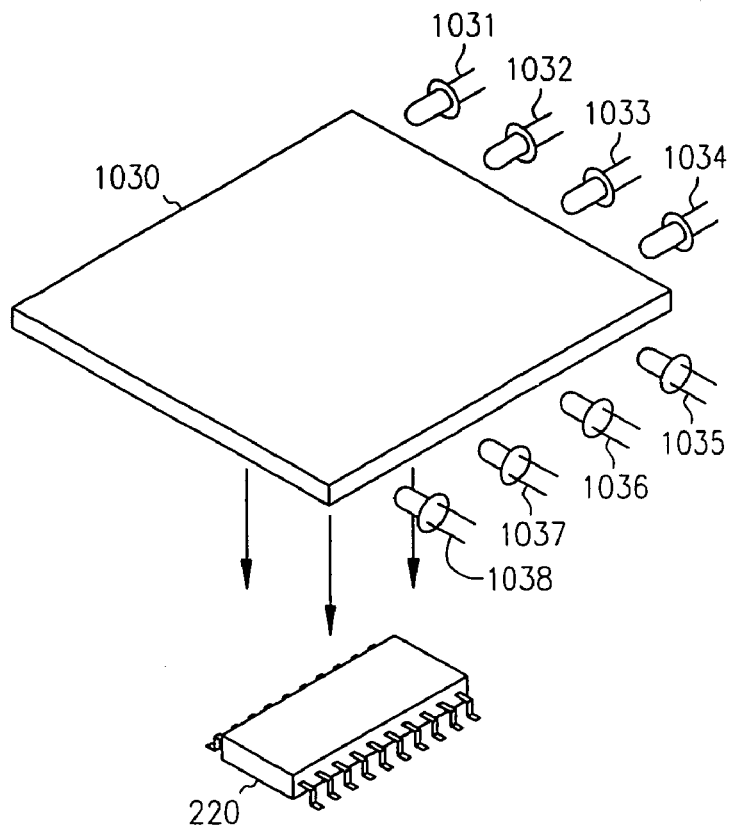
FIG. 10C is a perspective view of a third type of diffuser which can be used in the present invention.

Turning, now to FIGS. 10A, 10B and 10C, there are several different embodiments for illuminating the back lighting diffusers. In the first embodiment, FIG. 10A, there is an opaque diffuser 1010. The opaque diffuser 1010 includes a matte surface. It is front lit by LEDs 1012, 1014 to illuminate the diffuser to provide back lighting with respect to the device under test. As shown in FIG. 10B, a diffuser 1020 is formed of a translucent material that also has a matte finish. In this case, a set of LEDs 1022, 1023, 1024, 1025 are positioned behind the diffuser 1020. In other words, the translucent matte diffuser 1020 is positioned between the LEDs 1022, 1023, 1024, 1025 and the device under test 220. FIG. 10C shows another embodiment of a diffuser 1030. In this particular embodiment, LEDs 1031, 1032, 1033, 1034, 1035, 1036, 1037 and 1038 are positioned along the edges of the diffuser 1030, thus edge lighting the diffuser from within provides the backlighting for the device under test 220.

Figure 11A:
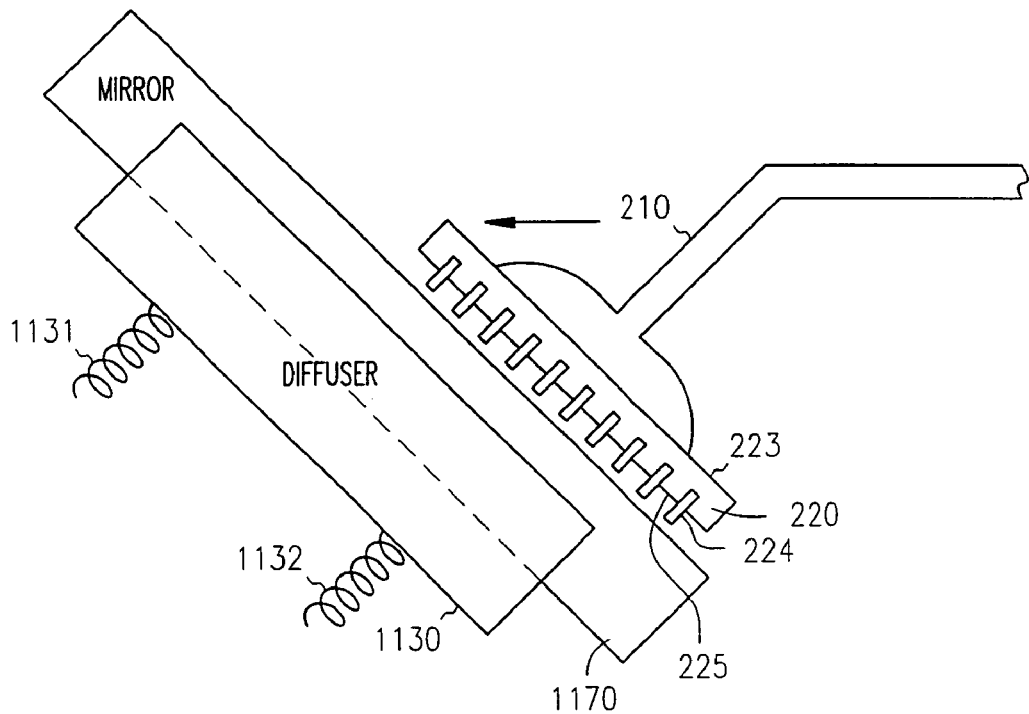
FIG. 11 is a schematic view of an embodiment of the present invention wherein the device under test is brought into contact with the diffuser at an angle.
Figure 11B:
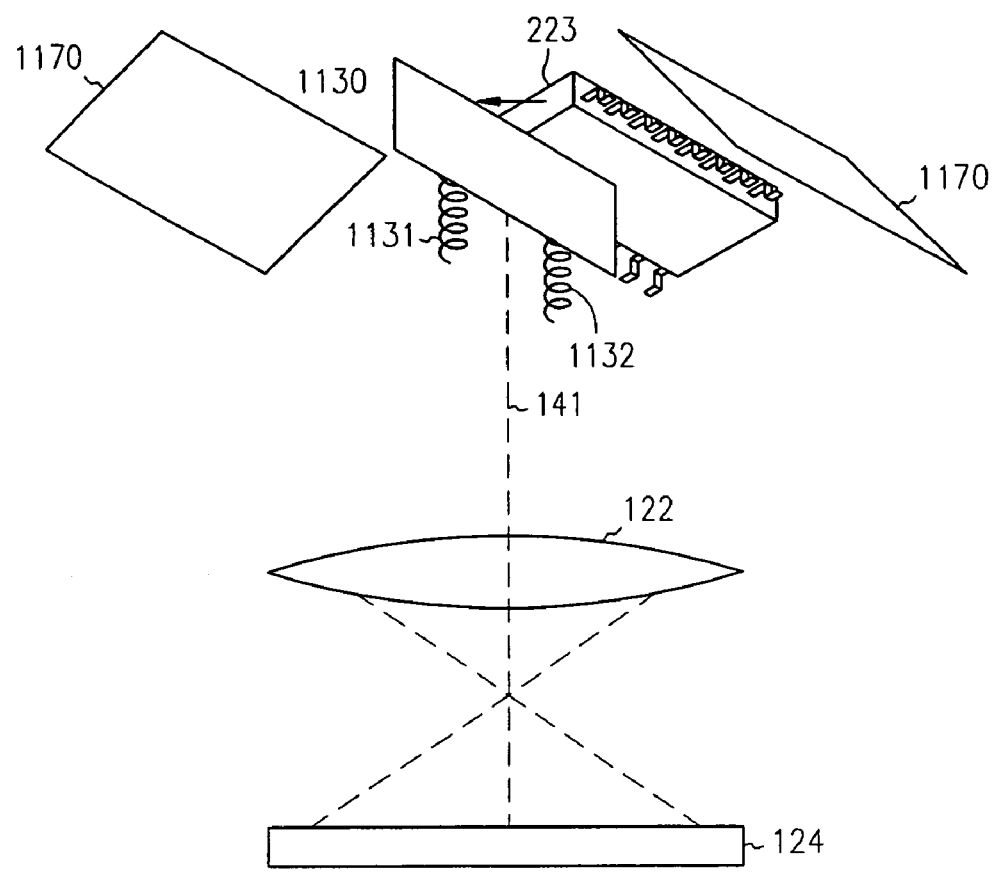
Figure 11C:
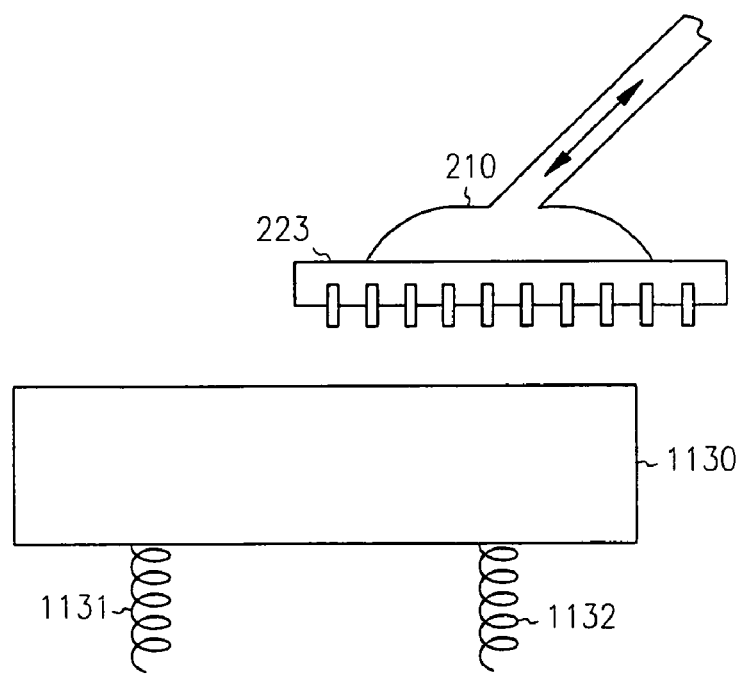

FIGS. 11A, 11B, and 11C are schematic views of an embodiment of the present invention wherein the device under test is brought into contact with a diffuser at an angle. As shown in side view FIG. 11A, there is a diffuser 1130 and a mirror 1170. The mirror and the diffuser are kept at the same relative angle so that the path lengths for the light paths are kept substantially the same to cut down on potential problems and differences in focal length of the images obtained. The device under test 220, which includes a first major surface 223 and a second major surface 225, is brought into the diffuser at a pitched angle. Diffuser 1130 is spring loaded, as depicted by the springs 1131, 1132, so that as the pick-and-place unit 210 brings the device under test 220 into contact with the diffuser, the diffuser is biased toward the major surface 225 of the device under test and ultimately will contact or substantially the contact the major surface 225 of the device under test 220. FIG. 11B shows a perspective view of the same configuration. FIG. 11C shows an equivalent configuration where the part and top edge of diffuser 1130 are horizontal, and are brought into contact at a pitched angle.

Figure 12A:
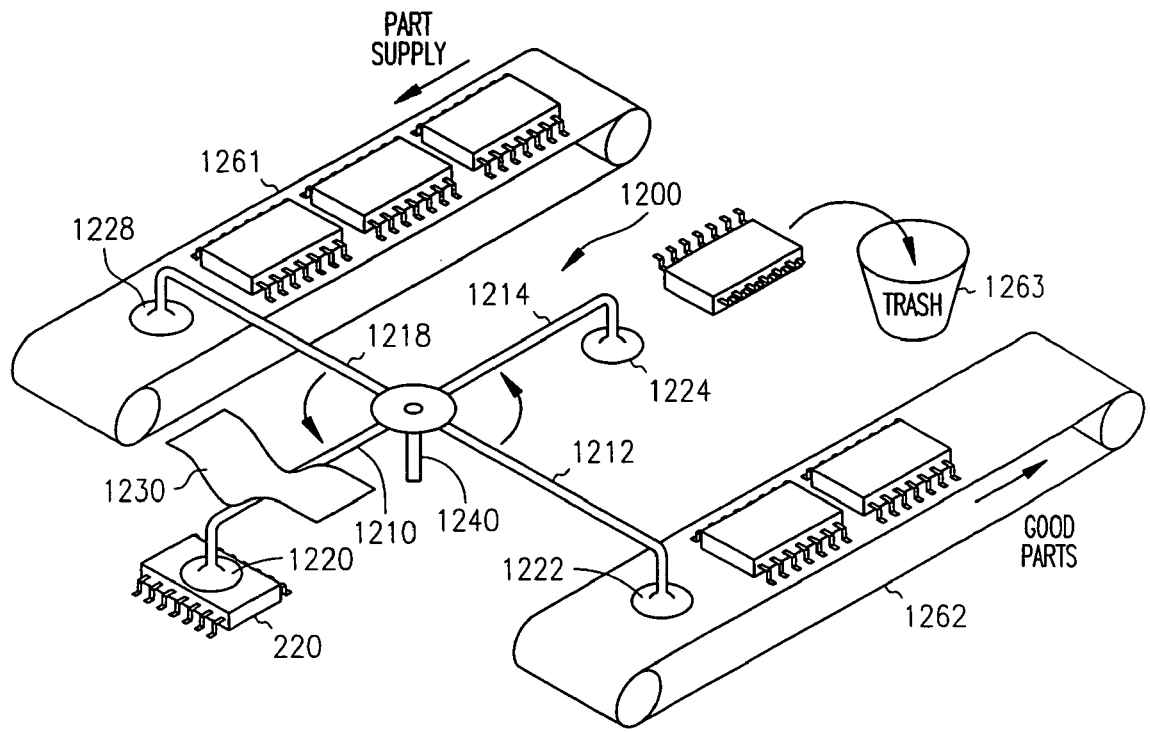
FIG. 12A is a perspective view of a set of pickers and a cam surface and diffuser used to land a device under test with respect to a diffuser.
Figure 12B:
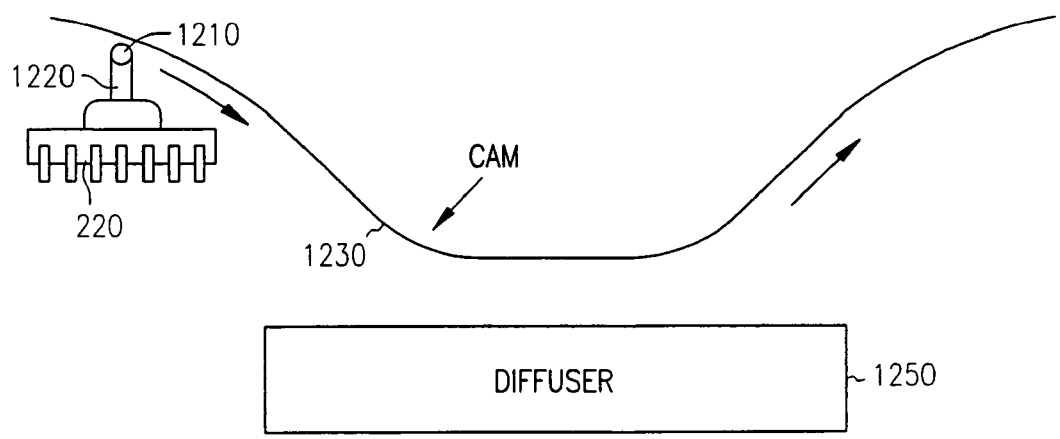
FIG. 12B is a schematic view of a diffuser cam surface, a picker carrying a device under test and a diffuser.

FIGS. 12A and 12B show an embodiment of a pick-and-place device that is capable of picking and placing multiple devices under test and bringing them in at a pitched angle. As shown in FIG. 12A, the pick-and-place device includes several vacuum tubes 1210, 1212, 1214, 1218. In addition, the pick-and-place device 1200 includes several vacuum pickup ends 1220, 1222, 1224, and 1228. The pick-and-place device 1200 also includes a cam-shaped surface 1230. The pick-and-place device rotates on a central axis 1240. The vacuum tubes are made of a flexible material so that the vacuum tubes of the pick-and-place machine can deflect as they go under the cam surface 1230 when a device under test is attached to the particular vacuum pickup area such as 1220. FIG. 12B shows and end view of the relationship between one arm 1210 of the pickup device 1200 and the cam surface 1230. The arm 1210, which also serves as the vacuum tube, rides on the cam surface so that it is positioned with respect to the diffuser 1250. Devices under test can then be attached to the adjacent arm so that after a test or image is acquired, the next device to be examined, is then moved in position underneath the cam surface and positioned correctly with respect to the diffuser 1250. Parts 220 can be successively picked up from a supply conveyor 1261, and good parts deposited to conveyor 1262, and bad parts to trash cam 1263.

Figure 13A:
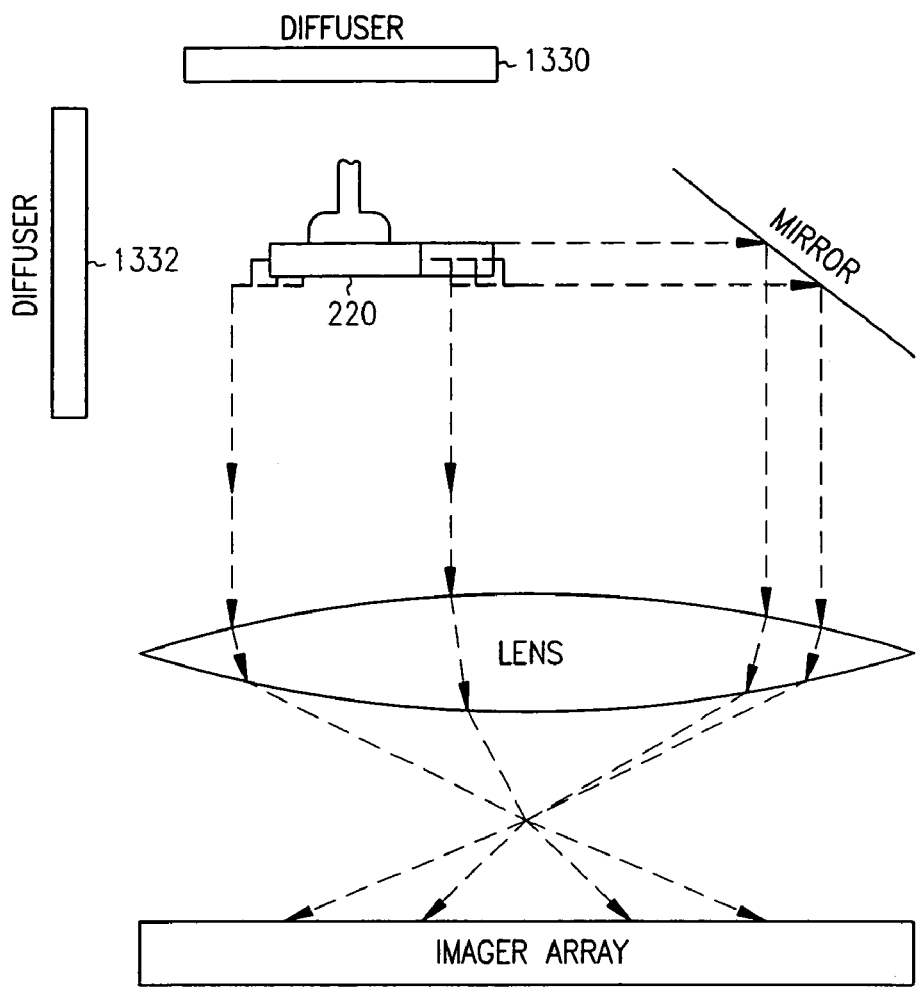
FIG. 13A is a schematic view of a device under test or object carried in a skewed orientation by a picker.
Figure 13B:
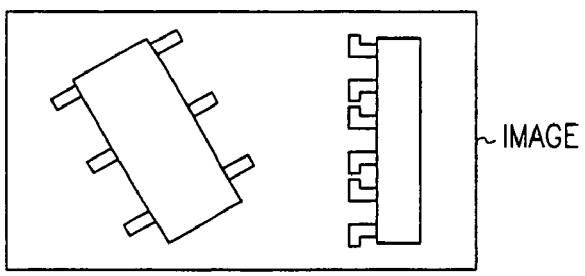
FIG. 13B is a representation of the view received at the imager in FIG. 13A.

FIG. 13 shows another method for acquiring an image. In this particular embodiment, the device under test is skewed so that features on both sides or at a different distance can be also viewed. The skew angle is selected so that each of the leads or features can be seen independently and so that the outline that results is not the result of shadows of something behind a particular lead. A side diffuser 1332 is placed on one side of the device under test. A pick-and-place machine skews the device under test 220. The top-down view is acquired from a diffuser on the top 1330. The side view is backlit via a diffuser 1332 on the left-hand side of the part. The image acquired is shown in FIG. 13B. The footprint of the object can be checked from the skewed image. The co-planarity of the leads or co-planarity of the part can be obtained from the single side view. LEDs are used to back light each of the diffusers 1330, 1332.

Figure 14:
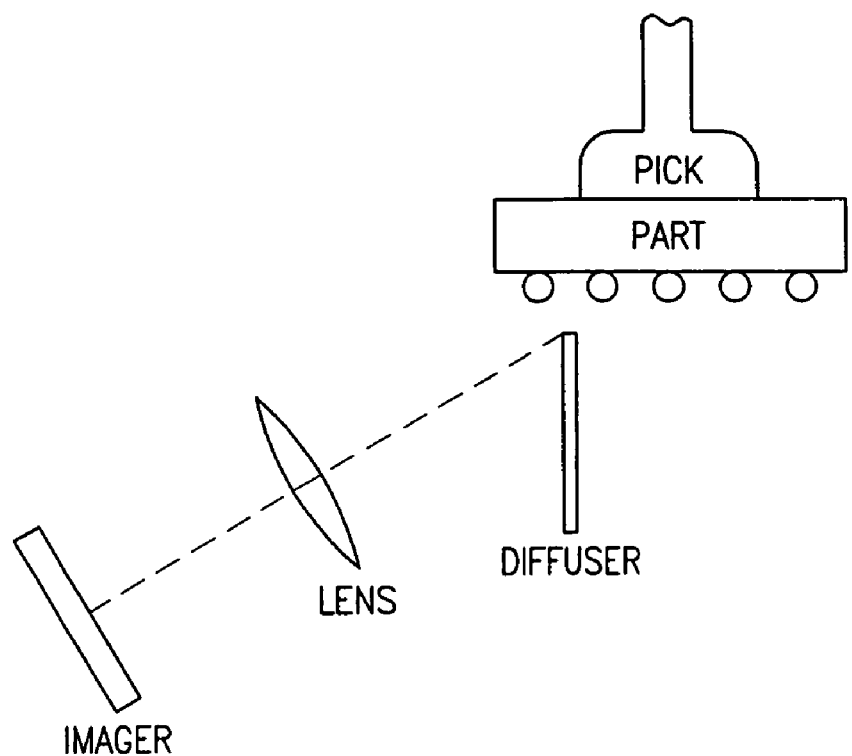
FIG. 14 is a schematic view of the imaging system in which the device under test is moved to one of several positions with respect to the diffuser so that various features may be seen on the device under test.

Another embodiment is shown in FIG. 14. In embodiment 1400, a pick-and-place machine 210 carries the part 220. The diffuser movement is actually stepped or moved, or the part is stepped or moved over the diffuser, so that the diffuser is successively placed behind each row of features, so that one successive row of features or one feature is viewed and imaged at each incremental movement. Described above are various other aspects and embodiments of the invention.

Figure 15:
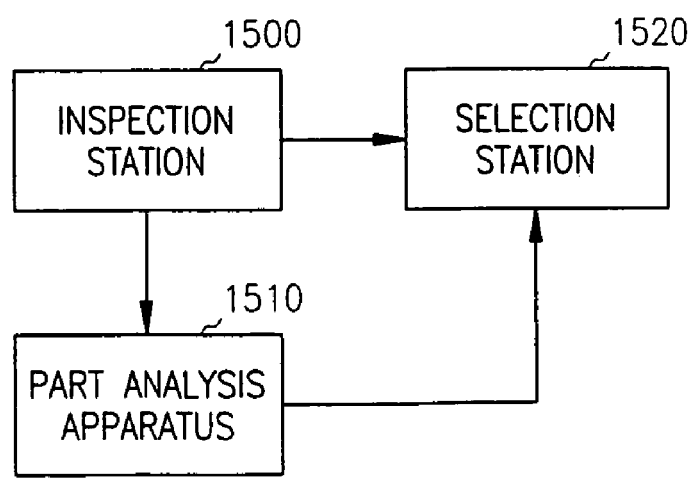
FIG. 15 is a schematic view of a system which includes an inspection system, a selection station and a part analysis apparatus as used in this invention.

Now turning to FIG. 15, there is shown a schematic diagram of the entire inspection system. The inspection system includes an inspection station 1500 which includes one of the embodiments used to determine whether the footprint of the part is proper and also to inspect the co-planarity of the leads. It should be understood that it is not necessary that electronic parts are what is inspected, other things could also be inspected to determine if they are within proper ranges. The inspection station obtains the images of the device under test 220. These images are then forwarded to a parts analysis apparatus 1510. The parts analysis apparatus determines if the part of the device under test passes inspection. The output of the parts analysis apparatus is fed to a selection station 1520. At the selection station, the part is either rejected or accepted. Rejected parts are placed into a separate bin for either total rejection or rework, while the accepted parts are placed into other bins or placed onto a circuit board as part of a final assembly of another bigger electronic device or bigger device.

Advantageously, the machine-vision system of the present invention can view a device under test using backlighting to minimize or substantially eliminate the problems associated with gathering useful data from images having specular reflections. The machine vision system of the present invention can accurately measure selected portions of a device under test. In addition, the machine vision system of the present invention isolates selected portions of a device under test to assure the accuracy of measurements made on the part. Yet another advantage is that one camera produces an image with all the desired views, including side views of the device under test for checking the co-planarity and a top-down view for checking that the geometry of the device under test will fit a corresponding set of pads on a circuit board. The machine vision system allows automated, high-speed, two-dimensional inspection of objects or devices under test.

CONCLUSION

In conclusion, several aspects of the invention are disclosed.

One aspect of the invention provides a machine-vision system for imaging an object, the object having a first side and a second side. This machine-vision system includes an imager, and an optics apparatus that images two or more views of the first side of the object without interference from the second side of the object.

In some embodiments, the two or more views of the first side of the object are from orthogonal angles.

In some embodiments, the optics apparatus further images two or more views of the second side of the object and wherein the two or more views of the second side of the object are from different angles.

In some embodiments of the system, the object includes a first major surface, the system further including a divider background surface placed at or near the first major surface of the object in order to obtain separate images of features of the object only on the first side of the object and features of the object only on the second side of the object.

In some embodiments, the divider is opaque, and the system further includes an LED lighting system that projects light from a plurality of LEDs onto the opaque divider.

In some embodiments, the divider background surface diffuses light to back light the features on the object on the first side and diffuses light to back light the features on the second side of the object.

In some embodiments, the object includes at least a first major surface, the system further including a divider background surface that contacts the first major surface of the object in order to obtain separate images of features of the object only on the first side of the object and of features of the object only on the second side of the object. In some such embodiments, the divider background surface diffuses light to back light the features on the object on the first side and diffuses light to back light the features on the second side of the object. In some embodiments, the divider is spring loaded to bias the divider against the object when the divider contacts the object.

In some embodiments, the optics apparatus includes an optical path folding optics that at least provides backlit and substantially orthogonal first and second views of the first side of the object and backlit and substantially orthogonal first and second views of the second side of the object, and includes a substantially non-transparent divider background surface placed in a relationship at or near the object in order block, from one of the views of the first side of a portion of the object, some portion of the second side of the object. The system further includes an LED lighting system that projects light from a plurality of LEDs onto the divider, and an information handling apparatus connected to the imager in order to receive image information from the imager, wherein the information handling apparatus determines co-planarity information of features of the object using the image information from the first and second views of the first side of the object and the first and second views of the second side of the object, and outputs data indicative of the co-planarity information.

In some embodiments, the divider includes an edge for contacting the major surface of the object, the edge of the divider initially forming an acute angle with respect to the major surface of the object.

In some embodiments of the system, the divider is biased so that the edge of the divider is substantially in parallel with the major surface of the object after initially forming an acute with the major surface of the object.

In some embodiments of the system, the object is moved both vertically and horizontally with respect to the major surface of the object.

Some embodiments of the system further include a picker for picking and moving objects.

In some embodiments of the system, one of the views of the first side and the second side are within a single image on the imager.

In some embodiments of the system, the single view is a top view of the object showing the first side and the second side of the object.

Some embodiments of the system further include an information-handling system that measures dimensions associated with the top view of the object.

In some embodiments of the system, one of the views of the first side and the second side are within a single image on the imager.

In some embodiments of the system, the single view is a top view of the object showing the first side and the second side of the object.

Some embodiments of the system further include an information-handling system that measures dimensions associated with the top view of the object from the obtained images.

Another aspect of the invention provides a machine-vision system for inspecting an object, the object having a first side and a second side. This machine-vision system includes an imager, and an optics apparatus that images a top-down view of the object that includes both the first side and the second side of the object, a separate first-side view of only the first side of the object and a separate second-side view of only the second side of the object.

In some embodiments, the optics apparatus includes a single camera that obtains the top-down view, the first side view and the second side view.

In some embodiments, the object includes at least one major surface, the machine vision system further including a divider background surface placed near the at least one major surface of the object in order to obtain the separate image of the first side of the object and the separate image of the second side of the object.

In some embodiments, the optics apparatus further includes a first reflective surface for obtaining the separate view of only the first side of the object, and a second reflective surface for obtaining the separate view of only the second side of the object.

Some embodiments of the system further include a base, at least one spring attaching the divider to the base, and a picker for picking and moving objects.

In some embodiments, the picker moves the object at an angle with respect to an edge of the divider.

In some embodiments of the system, the top-down view of the object that includes both the first side and the second side of the object, the separate view of the first side of the object, and the separate view of the second side of the object are backlit.

In some embodiments of the system, wherein the top-down view of the object that includes both the first side and the second side of the object, the separate view of the first side of the object, and the separate view of the second side of the object are backlit.

Some embodiments of the system further include a measurement apparatus for determining dimensions on at least one of the top-down view of the object that includes both the first side and the second side of the object, the separate view of the first side of the object, and the separate view of the second side of the object.

Another aspect of the invention provides a method for obtaining a machine-vision image of an object including blocking a first portion of the object with a first illuminated surface, and imaging a second portion of the object using back light from the first illuminated surface.

In some embodiments, the method further includes blocking the second portion of the object with a second illuminated surface, and imaging the first portion of the object using back light from the second illuminated surface.

In some embodiments, the method further includes imaging an outline of at least a portion of the object using back light form a third illuminated surface.

In some embodiments, the method further includes obtaining digitized image information about the first portion of the object and the second portion of the object, determining co-planarity information of features the first portion of the object and the second portion of the object using the digitized image information, and outputting data indicative of the co-planarity information.

In some embodiments, the method further includes sorting the object into one of a plurality of output groups based on the co-planarity information.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A machine-vision system for imaging an object, the object having a first set of projecting features and a second set of projecting features, the machine-vision system comprising:
    an imager;
    a diffuser divider background device that is positionable between the first set of projecting features and the second set of projecting features to block a view of the second set of features and wherein the background device is along an optical axis of the imager between the object and the imager when the imager obtains its image data; and
    an optics apparatus that images a view of the first set of projecting features to the imager with the background device blocking the view of the second set of projecting features.

2. The system of claim 1, wherein two or more simultaneous backlit views of the first set of projecting features of the object are obtained in a single image by the optics apparatus and the imager.

3. The system of claim 2, wherein the optics apparatus further obtains two or more simultaneous views of the second set of projecting features of the object into the imager, and wherein the two or more views of the second set of projecting features of the object are from different angles.

4. The system of claim 1, wherein an edge of the divider background surface is placed near a first major surface of the object in order to obtain separate images of features of the object only on a first side of the divider background surface and features of the object only on a second side of the divider background surface.

5. The system of claim 4, further comprising
    an illumination unit that directly illuminates the divider background device to provide backlighting of the first set of features.

6. The system of claim 1, wherein the object includes at least a first major surface, wherein the divider background device is spring-loaded and the divider background device contacts the first major surface of the object in order to obtain separate images of features of the object only on the first side of the divider background surface and of features of the object only on the second side of the divider background surface.

7. The system of claim 6, wherein the divider is opaque.

8. The system of claim 1, further comprising
an illumination unit that directly illuminates the divider background device without a light-diminishing surface in the light path between the illumination unit and the divider background, in order to provide backlighting of the first set of features.

9. The system of claim 1, wherein no device that substantially reduces an amount of light is located in the optical path between the first set of features and the optics apparatus that images the view.

10. The system of claim 1, wherein the divider background device includes an elastomeric material.

11. The system of claim 1, wherein the object is brought into contact with the diffuser at a pitched angle.

12. A machine-vision system for use with a computer-machine-vision system for imaging an object, the object having a first set of projecting features and a second set of projecting features, the machine-vision system comprising:
a divider background device that is positionable between the first set of projecting features and the second set of projecting features to block a view of the second set of features; and
an optics apparatus that forms an image having a view of the first set of projecting features with the background device blocking the view of the second set of projecting features,
wherein an edge of the divider background surface is placed at least close enough to a first major surface of the object in order to obtain separate images of features of the object only on a first side of the divider background surface and features of the object only on a second side of the divider background surface, and
a diffuser-part movement unit operable to move the part and diffuser relative to one another, so that the diffuser is placed between a first pair of rows, each row having one or more features, so that an image is acquired of at least one row of the first pair with the diffuser providing backlighting to the at least one row of the first pair, and the movement unit is operable to later move the part and diffuser relative to one another, so that the diffuser is placed between a second pair of rows, each row having one or more features, so that an image is acquired of at least one row of the second pair with the diffuser providing backlighting to the at least one row of the second pair.

13. The system of claim 12, wherein the object is brought into contact with the divider background device at a pitched angle.

14. A method for obtaining a machine-vision image of an object comprising:
providing an object that has a first portion having projecting features and a second portion having projecting features;
providing a diffuser divider background with a first diffuser surface and a second diffuser surface;
providing an imager;
positioning the diffuser divider background between the first portion's projecting features and the second portion's projecting features with the object along an optical axis of the imager and further from the imager than is the divider background;
blocking a view of the first portion's projecting features with the first diffuser surface; and
imaging the second portion's projecting features with the imager using the first diffuser surface as a background.

15. The method of claim 14, further comprising:
directly illuminating the first surface, wherein the imaging of the second portion uses backlighting from the illuminated first surface.

16. The method of claim 14, further comprising:
blocking the second portion of the object with the second diffuser surface; and
imaging the first portion of the object using backlighting from the second surface as a background.

17. The method of claim 16, further comprising:
illuminating the second surface, wherein the imaging of the first portion uses backlighting from the illuminated second surface.

18. The method of claim 17, further comprising:
obtaining digitized backlit image information about the first portion of the object and the second portion of the object;
determining co-planarity information of features of the first portion of the object and the second portion of the object using the digitized image information; and
outputting data indicative of the co-planarity information.

19. The method of claim 16, further comprising:
obtaining digitized backlit image information about the first portion of the object and the second portion of the object;
determining co-planarity information of features of the first portion of the object and the second portion of the object using the digitized image information; and
outputting data indicative of the co-planarity information.

20. The method of claim 14, further comprising:
bringing the object into contact with the diffuser at a pitched angle.

21. A system for obtaining a machine-vision image of an object having a first portion having projecting features and a second portion having projecting features, the system comprising:
first means for blocking a view of a first portion of the object, wherein the first means for blocking includes a first diffuser surface;
means for positioning the first means for blocking between the first portion of projecting features and the second portion of projecting features; and
means for imaging the second portion's projecting features using the first diffuser surface as a background wherein the first means for blocking is located between the object and the means for imaging when the image is obtained.

22. The system of claim 21, further comprising:
means for directly illuminating the first means for blocking, wherein the means for imaging of the second portion uses backlighting from the illuminated first means for blocking.

23. The system of claim 21, further comprising:
second means for blocking the second portion of the object, wherein the second means for blocking includes a second diffuser surface; and
means for imaging the first portion of the object using the second diffuser surface as a background.

24. The system of claim 23, further comprising:
means for illuminating the second means for blocking, wherein the means for imaging of the first portion uses backlighting from the illuminated second means for blocking; and means for obtaining simultaneous backlit views of the second portion of the object.

25. The system of claim 24, further comprising:

means for obtaining digitized backlit image information about the first portion of the object and the second portion of the object;

means for determining co-planarity information of features of the first portion of the object and the second portion of the object using the digitized image information; and an output device, operatively coupled to the means for determining, that outputs data indicative of the co-planarity information.

26. The system of claim 23, further comprising:

means for obtaining digitized backlit image information about the first portion of the object and the second portion of the object;

means for determining co-planarity information of features of the first portion of the object and the second portion of the object using the digitized image information; and an output device, operatively coupled to the means for determining, that outputs data indicative of the co-planarity information.

27. The system of claim 21, further comprising:

means for bringing the first means for blocking into contact with the object at a pitched angle.

* * * * *